(12) United States Patent
Kern et al.

(10) Patent No.: US 10,661,072 B2
(45) Date of Patent: May 26, 2020

(54) TENS ATTACHMENT FOR DEVICE FOR CLEANSING AND TREATING SKIN

(71) Applicant: NSE Products, Inc., Provo, UT (US)

(72) Inventors: Dale G. Kern, Hyde Park, UT (US); Kevin S. Oberkramer, Placentia, CA (US); Jared H. Nathanson, Mission Viejo, CA (US); Robert D. Miller, Costa Mesa, CA (US); Paul J. Gleason, Laguna Niguel, CA (US)

(73) Assignee: NSE Products, Inc., Provo, UT (US)

( * ) Notice: Subject to any disclaimer, the term of this patent is extended or adjusted under 35 U.S.C. 154(b) by 176 days.

(21) Appl. No.: 15/990,075

(22) Filed: May 25, 2018

(65) Prior Publication Data

US 2018/0361137 A1 Dec. 20, 2018

Related U.S. Application Data

(60) Provisional application No. 62/511,141, filed on May 25, 2017.

(51) Int. Cl.
*A61N 1/04* (2006.01)
*A46B 13/02* (2006.01)
(Continued)

(52) U.S. Cl.
CPC .......... *A61N 1/0456* (2013.01); *A46B 13/008* (2013.01); *A46B 13/02* (2013.01);
(Continued)

(58) Field of Classification Search
None
See application file for complete search history.

(56) References Cited

U.S. PATENT DOCUMENTS

| 1,913,462 A | 6/1933 | Timar |
| 2,480,023 A | 8/1949 | Holden |

(Continued)

FOREIGN PATENT DOCUMENTS

| DE | 17 57 913 | 6/1971 |
| DE | 20103026.8 U1 | 8/2001 |

(Continued)

OTHER PUBLICATIONS

PCT, "International Preliminary Report on Patentability", Application No. PCT/US2015/045040, dated Nov. 24, 2015, 13 pages.
(Continued)

*Primary Examiner* — Brian T Gedeon
(74) *Attorney, Agent, or Firm* — Dorsey & Whitney LLP

(57) ABSTRACT

A device for delivery of TENS current, attachable to a handheld skin treatment device with a mechanical motion source, comprises a housing for mounting on the handheld skin treatment device, with a conductive skin contact head with first and second electrodes for receiving a TENS signal as a voltage established between the electrodes and a connector mounted in or on the housing and configured to interface with the mechanical motion source to receive the motion of the motion source. The device has an energy converter in the housing to convert the motion into electrical current, a power control circuit for receiving the electrical current and converting it into at least one power supply output voltage; and a signal generation circuit connected to the at least one the power supply output voltage for producing as an output a TENS signal for delivery to skin.

17 Claims, 16 Drawing Sheets

(51) Int. Cl.
*A61N 1/32* (2006.01)
*A61H 7/00* (2006.01)
*A61H 23/02* (2006.01)
*A46B 15/00* (2006.01)
*A46B 13/00* (2006.01)

(52) U.S. Cl.
CPC ........ *A46B 13/023* (2013.01); *A46B 15/0022* (2013.01); *A61H 7/005* (2013.01); *A61H 23/02* (2013.01); *A61N 1/322* (2013.01); *A61N 1/328* (2013.01); *A46B 2200/1006* (2013.01)

(56) References Cited

U.S. PATENT DOCUMENTS

| | | |
|---|---|---|
| 2,682,675 A | 7/1954 | Prucha |
| 2,764,773 A | 10/1956 | Glanvill et al. |
| 3,906,940 A | 9/1975 | Kawada |
| 3,968,789 A | 7/1976 | Simoncini |
| 4,027,348 A | 6/1977 | Flowers et al. |
| 4,033,356 A * | 7/1977 | Hara ............... A61N 1/0452 607/152 |
| 4,249,521 A | 2/1981 | Gueret |
| D262,672 S | 1/1982 | Iten et al. |
| 4,343,265 A | 8/1982 | Belschner |
| 4,463,485 A | 8/1984 | Gueret |
| D285,131 S | 8/1986 | Wilkeson |
| D321,434 S | 11/1991 | Strickler |
| 5,176,130 A | 1/1993 | Kim |
| D333,730 S | 3/1993 | Martin |
| D333,922 S | 3/1993 | Strickler et al. |
| 5,228,165 A | 7/1993 | Westberry et al. |
| D342,319 S | 12/1993 | Cheng |
| D344,137 S | 2/1994 | Yoo |
| D351,947 S | 11/1994 | Fitzgerald |
| D357,322 S | 4/1995 | Matthews |
| D368,343 S | 3/1996 | Gebhard et al. |
| D369,447 S | 4/1996 | Kubes et al. |
| D370,124 S | 5/1996 | Chamieh |
| D409,337 S | 5/1999 | Johnson |
| 6,076,222 A | 6/2000 | Jolly |
| 6,267,736 B1 | 7/2001 | McCambridge et al. |
| D460,554 S | 7/2002 | Park |
| 6,424,862 B1 | 7/2002 | Brown, III et al. |
| D462,483 S | 9/2002 | Campbell |
| 6,588,964 B1 | 7/2003 | Au et al. |
| D479,336 S | 9/2003 | La et al. |
| D485,990 S | 2/2004 | Wallace |
| 6,801,808 B2 * | 10/2004 | Lee ............... A61N 1/32 607/115 |
| D514,328 S | 2/2006 | Huang |
| D523,962 S | 6/2006 | Huang |
| 7,194,316 B2 | 3/2007 | Bousfield et al. |
| D539,916 S | 4/2007 | Baldachini |
| D545,970 S | 7/2007 | Eknoian et al. |
| D545,971 S | 7/2007 | Eknoian et al. |
| D548,339 S | 8/2007 | Stonier et al. |
| D555,407 S | 11/2007 | Lan |
| 7,320,691 B2 | 1/2008 | Pilcher et al. |
| D567,387 S | 4/2008 | Nan |
| 7,384,377 B2 | 6/2008 | Berman |
| 7,386,906 B2 | 6/2008 | Roth et al. |
| 7,395,110 B2 | 7/2008 | Hofmann et al. |
| D589,257 S | 3/2009 | Van |
| 7,786,626 B2 | 8/2010 | Reishus et al. |
| D636,933 S | 4/2011 | Newman |
| D646,795 S | 10/2011 | Seehoff et al. |
| D661,811 S | 6/2012 | Ferguson et al. |
| 8,271,090 B1 | 9/2012 | Hartman et al. |
| D671,281 S | 11/2012 | Singer |
| D682,497 S | 5/2013 | Wargo et al. |
| 8,523,791 B2 | 9/2013 | Castel |
| D699,903 S | 2/2014 | Singer |
| 8,679,039 B2 | 3/2014 | Tieu et al. |
| 8,745,807 B2 | 6/2014 | Varner et al. |
| D711,656 S | 8/2014 | Brewer et al. |
| D715,553 S | 10/2014 | Brewer et al. |
| D720,933 S | 1/2015 | Albers |
| 8,945,104 B2 * | 2/2015 | Boone, III ............ A61H 9/0057 606/9 |
| 8,954,155 B2 * | 2/2015 | Campbell ............ A61N 1/0476 607/50 |
| D726,418 S | 4/2015 | Gruber et al. |
| 9,032,576 B2 | 5/2015 | Zelickson et al. |
| D734,949 S | 7/2015 | Behnam |
| D740,033 S | 10/2015 | Gruber et al. |
| D749,325 S | 2/2016 | Middendorp |
| 9,272,141 B2 * | 3/2016 | Nichols ............... A61H 7/005 |
| D753,399 S | 4/2016 | Owen et al. |
| D753,400 S | 4/2016 | Khoun et al. |
| 9,301,657 B2 | 4/2016 | Miller et al. |
| D768,391 S | 10/2016 | Kling et al. |
| D778,064 S | 2/2017 | Owen et al. |
| D778,065 S | 2/2017 | Kern et al. |
| D778,066 S | 2/2017 | Kern et al. |
| D781,588 S | 3/2017 | Lee |
| D782,197 S | 3/2017 | Kern et al. |
| D795,593 S | 8/2017 | Huang |
| D796,212 S | 9/2017 | Thornton |
| D797,461 S | 9/2017 | Dandridge et al. |
| D803,572 S | 11/2017 | Nichols |
| 10,080,428 B2 | 9/2018 | Kern |
| D829,445 S | 10/2018 | Kern et al. |
| 2002/0156402 A1 * | 10/2002 | Woog ............... A61H 23/0236 601/46 |
| 2005/0059914 A1 | 3/2005 | Kleinhenz et al. |
| 2005/0113725 A1 | 5/2005 | Masuda |
| 2005/0142093 A1 | 6/2005 | Skover et al. |
| 2005/0277950 A1 | 12/2005 | Pilcher et al. |
| 2005/0278877 A1 | 12/2005 | Akridge et al. |
| 2006/0010630 A1 | 1/2006 | Tse |
| 2006/0058714 A1 | 3/2006 | Rhoades |
| 2006/0276731 A1 | 12/2006 | Thiebaut et al. |
| 2007/0142845 A1 | 6/2007 | Akridge et al. |
| 2007/0179412 A1 | 8/2007 | Imboden et al. |
| 2007/0276449 A1 | 11/2007 | Gunter et al. |
| 2008/0005860 A1 | 1/2008 | Niizaki et al. |
| 2008/0119913 A1 | 5/2008 | Powell et al. |
| 2008/0125682 A1 | 5/2008 | Bonneyrat |
| 2008/0167590 A1 | 7/2008 | Jon et al. |
| 2008/0222822 A1 | 9/2008 | Cobabe et al. |
| 2008/0295268 A1 | 12/2008 | Lei |
| 2009/0198159 A1 | 8/2009 | Linzell |
| 2009/0318853 A1 | 12/2009 | Reed et al. |
| 2010/0217357 A1 | 8/2010 | Da et al. |
| 2010/0262051 A1 | 10/2010 | De |
| 2010/0292746 A1 | 11/2010 | Gorham |
| 2011/0118655 A1 | 5/2011 | Fassih et al. |
| 2011/0184499 A1 | 7/2011 | Radi |
| 2011/0251537 A1 | 10/2011 | Yeo |
| 2012/0121313 A1 | 5/2012 | Thiebaut |
| 2012/0165708 A1 | 6/2012 | Parsloe |
| 2012/0165710 A1 | 6/2012 | Nichols |
| 2012/0209151 A1 | 8/2012 | Zhou et al. |
| 2013/0023805 A1 | 1/2013 | Ungemach et al. |
| 2013/0023806 A1 | 1/2013 | Ungemach et al. |
| 2013/0046212 A1 | 2/2013 | Nichols |
| 2013/0079689 A1 | 3/2013 | Thierman |
| 2015/0034113 A1 | 2/2015 | Yamagishi et al. |
| 2015/0265825 A1 | 9/2015 | Miller et al. |
| 2015/0305487 A1 | 10/2015 | Pardo et al. |
| 2015/0305969 A1 | 10/2015 | Giraud et al. |
| 2015/0359324 A1 | 12/2015 | Brewer |
| 2016/0045081 A1 | 2/2016 | Kern |
| 2016/0183670 A1 | 6/2016 | Brewer et al. |
| 2016/0206087 A1 | 7/2016 | Skidmore et al. |
| 2017/0049278 A1 | 2/2017 | Thomassen |
| 2017/0073050 A1 | 3/2017 | Smith |
| 2017/0112333 A1 | 4/2017 | Mccauley |

(56) References Cited

U.S. PATENT DOCUMENTS

| | | | |
|---|---|---|---|
| 2017/0189670 A1* | 7/2017 | Brunson | A61N 1/303 |
| 2018/0055720 A1* | 3/2018 | Sitkovetskiy | A61H 7/004 |

FOREIGN PATENT DOCUMENTS

| | | |
|---|---|---|
| DE | 20103026 U1 | 8/2001 |
| GB | 1208149 A | 10/1970 |
| JP | S55-062292 U | 10/1958 |
| JP | 2001293050 A | 10/2001 |
| JP | 2004249061 A | 9/2004 |
| JP | 2006061486 A | 3/2006 |
| JP | 2010524625 A | 7/2010 |
| JP | 2013106741 A | 6/2013 |
| WO | 03075712 A1 | 9/2003 |
| WO | 2004057999 A1 | 7/2004 |
| WO | 2008135953 A1 | 11/2008 |
| WO | 2009136911 A1 | 11/2009 |
| WO | 2013077284 A1 | 5/2013 |
| WO | 2013132363 A1 | 9/2013 |
| WO | 2013132364 A1 | 9/2013 |
| WO | 2014024084 A1 | 2/2014 |
| WO | 2014118596 A1 | 8/2014 |
| WO | 2016025702 A1 | 2/2016 |
| WO | 2017027793 A1 | 2/2017 |
| WO | 2018218183 A2 | 11/2018 |
| WO | 2018218183 A3 | 1/2019 |

OTHER PUBLICATIONS

PCT, "International Search Report", Application No. PCT/US2015/045040, dated Jan. 15, 2016, 7 pages.

International Preliminary Report on Patentability dated Feb. 22, 2018, for International Application No. PCT/US2016/046738, 8 pages.

International Search Report and Written Opinion for PCT/US2018/034714, dated Dec. 20, 2018, pp. 1-192.

International Search Report and Written Opinion dated Dec. 1, 2016, for International Application No. PCT/US2016/046738.

International Search Report dated Jan. 15, 2016 for PCT/US2015/045040 filed Aug. 13, 2015, 22 pages.

"Facemaster Platinum Instruction Manual", downloaded from https://www.facemaster.com/pages/manual-and-quick-start-guides-for-facemaster-microcurrent-machine on Jan. 22, 2019, pp. 9.

"Rejuvenique Facial Toning System #RJV10", from Salton, Inc., Aug. 8, 2001; 6 pages.

"TLV61220 Low-Input Voltage Step-Up Converter in Thin SOT-23 Package", Texas Instruments, May 2012, revised Dec. 2014, pp. 24.

FOREO, , "Face Scrub Brush & Anti Aging Skin Care", Face Scrub Brush & Anti Aging Skin Care | LUNA™ by FOREO downloaded from https://www.foreo.com/luna, Jan. 21, 2016, 5.

Jung, Woo-Suk et al., "Powerful curved piezoelectric generator for wearable applications", Nano Energy, Science Direct, vol. 13, Apr. 2015, ISSN 2211-2855, pp. 174-181, Apr. 1, 2015.

Moodie, , "Clinique Advocates 'fitness for the face'", The Moodie Report, "Clinique advocates 'fitness for the face' with new Sculptwear range", downloaded from https://www.moodiereport.com/document.php?doc_id=43808, Sep. 6, 2015, 2.

Proactive, , "Deep Cleansing Brush", Proactiv Advertisement—Deep Cleansing Brush, https://www1.proactiv.com, 1 page, date unknown.

Thakral, Gaurav et al., "Electrical stimulation to accelerate wound healing", Diabetic Foot & Ankle, 2013; 4:10.3402/dfa.v4i0.22081, 1-9.

XOUT, , "X Out Wash in Treatement", X Out Wash in Treatment—Acne Treatment for Teens | X Out™, downloaded from https://www.xout.com/specialoffer/, Oct. 27, 2015, 1.

\* cited by examiner

TENS ATTACHMENT FOR DEVICE FOR CLEANSING AND TREATING SKIN

CROSS-REFERENCE TO RELATED APPLICATIONS

This application claims the benefit of U.S. Provisional Application No. 62/511,141, filed May 25, 2017.

TECHNICAL FIELD

The invention relates to devices for cleansing and treating skin, particularly facial skin, and an attachment for delivery of TENS (Transcutaneous electrical nerve stimulation) from a device that uses mechanical action for cleansing and treating skin.

BACKGROUND

Skin is the largest organ of the human body, with several important functions, including forming a physical barrier to the environment, protection against micro-organisms, allowing and limiting the inward and outward passage of water and electrolytes, ultraviolent radiation and toxic agents. Within the skin there are three structural layers: the epidermis, the dermis and the subcutis. Keratinocytes are the main cell type found within the epidermis. Fibroblasts are the predominant cell type within the dermis. The dermis is composed of a supportive extracellular matrix and contains bundles of collagen which run parallel to the skin surface. The role of fibroblasts within the dermis is to produce collagen, elastin, and structural proteoglycans. The collagen fibers constitute 70% of the dermis, giving it strength and toughness, while elastin provides normal elasticity and flexibility. The proteoglycans provide viscosity and hydration. Transforming growth factor β (TGF-β) is associated with the regulation of extracellular matrix production in human skin connective tissue. This factor is also of importance in the process of wound healing. Skin also is innervated and vascularized, and also contains small numbers of immune cells (e.g. mast cells, tissue macrophages, etc.).

Aging of human skin is associated with discoloration, wrinkling, and the sagging effect. These developments related to aging are dramatically visible in human skin which becomes dry, wrinkled, lax, and irregularly pigmented over time. Typically, aged skin is characterized by a flattening of the dermal-epidermal junction, increased atrophy, and a loss of elasticity of the dermal connective tissue. The loss of firmness and elasticity is commonly associated with the decrease/loss and disorganization of the major extracellular components, including collagen I (associated with being the primary cause of wrinkle formation), elastin, and large and small proteoglycans and glycosaminoglycans. Aging skin also possesses decreased TGF-β which results in reduced production of collagen and compromised wound healing. A histological analysis of aging in human skin has revealed a decrease in tissue thickness, disorganization of collagen, and accumulation of non-functional elastin.

Handheld skin cleansing devices are used for cosmetic purposes to efficiently cleanse facial skin. In some cases the devices claim additional benefits, such as exfoliation, smoothing/resurfacing, or deep cleaning. Such devices have one or more discrete electrically powered bristle brushes or nonwoven fabric pads that oscillate, vibrate, or a combination thereof to provide mechanical action of the brush(es) or pad(s) against the skin. Typically, a cleanser is applied to the bristles or the pad. Cleansing effectiveness of these devices depends on the bristle or pad type, pressure applied, and the type of cleanser.

One example of many is the SonicDermabrasion Facial Brush ST255, sold by PRETIKA® Corp. of Laguna Hills, Calif. The brush includes a handle and a round bristle brush head that rotates. Another example is the Pore Sonic Cleanser sold by Pobling of Seoul, S. Korea, which includes an oblong brush that is vibrated. Further examples are found in U.S. Patent Application Publication 20160045081 for Device And Method For Cleansing And Treating Skin, Ser. No 14/825316 and Device And Method For Cleansing And Treating Skin, PCT Application No. PCT/US2016/046738. Many examples similar to these are easily found in department stores, drug stores, and online.

Such rotating and/or vibrating heads provide cleaning action that is superior to the use of hands to clean one's face. However, it may be desirable to add to such devices a further form of skin treatment. Use of TENS (Transcutaneous Electrical Nerve Stimulation) is known for wound healing. (See, "Electrical stimulation to accelerate wound healing", Gaurav Thakral, Javier LaFontaine, Bijan Najafi, Talal K. Talal, Paul Kim, Lawrence A. Lavery, Diabetic Foot & Ankle. 2013; 4: 10.3402/dfa.v4i0.22081. Published online 2013 Sep. 16. doi: 10.3402/dfa.v4i0.22081). There also exist TENS products that have been approved by the U.S. Food & Drug Administration for aesthetic skin application purposes, such as Rejuvenique Model #RJV10 from Salton, Inc.; Facial Toning System from Face Master; Nutritone from Isomera; and Trinity from Carol Cole—NuFace.

Skin that has been effectively cleansed may have its aesthetic aspects, such as presence of facial fine lines, mottled pigmentation, uneven skin tone, tactile roughness, global firmness appearance, and jaw-line contour, as well as desired attributes such as smoothness or radiance, improved. Accordingly, it may be desirable to provide aesthetic TENS treatment in combination with cleansing. Such treatment using electrical stimulation may be desirable to use in combination with a mechanical cleaning treatment, either before or after. The device described below shows in one or more embodiments how a TENS treatment feature may be added to certain types of handheld cleansing devices.

SUMMARY

Disclosed herein is an attachment for a cleansing device for delivery of TENS current. The attachment is attachable to a handheld skin treatment device with a mechanical motion source and comprises a housing for mounting on the handheld skin treatment device, with a conductive skin contact head with first and second electrodes for delivery to skin a TENS signal as a voltage established between the electrodes and a connector mounted in or on the housing and configured to interface with the mechanical motion source to receive the motion of the motion source. The device has an energy converter in the housing to convert the motion into electrical current, a power control circuit for receiving the electrical current and converting it into at least one power supply output voltage; and a signal generation circuit connected to the at least one the power supply output voltage for producing as an output the TENS signal for delivery to skin.

In various embodiments, the device converts either oscillatory or rotating motion into electrical current by using a stepper motor generator driven with either oscillating or rotating motion or by rotating a rotating motor generator.

In one embodiment, the handheld skin treatment device has a mechanical motion source and a jack connector and comprises: a housing for mounting on the handheld skin treatment device, comprising a conductive skin contact head with first and second electrodes for receiving a TENS signal as a voltage established between them; a connection jack mounted in or on the housing and configured for insertion in the connection jack to interrupt a current that powers the motion source and to direct a current from an electrical power source of the handheld skin treatment device to a current supply pair leading into the TENS attachment; and a signal generation circuit connected to the current supply pair for producing as an output a TENS signal for delivery to skin.

Also disclosed herein is a skin cleansing system including a device with a handle; an electrical motor disposed within the handle and attached to an actuator, said motor and actuator adapted to apply an oscillating or other movement and an attachment that converts the movement to electrical signals that are known to be useful for TENS. The TENS may then be supplied from the same handheld base. It may be used with a cleanser, conduction improver or other skin benefitting substance selected from the group consisting of a liquid, dispersion, lotion, gel, serum, or solution applied to a skin surface that has previously received or will later receive an oscillating, rotating or other cleansing movement of a cleansing head.

Additional advantages and novel features of the device will be set forth in part in the description that follows.

DETAILED DESCRIPTION

Figure 1:
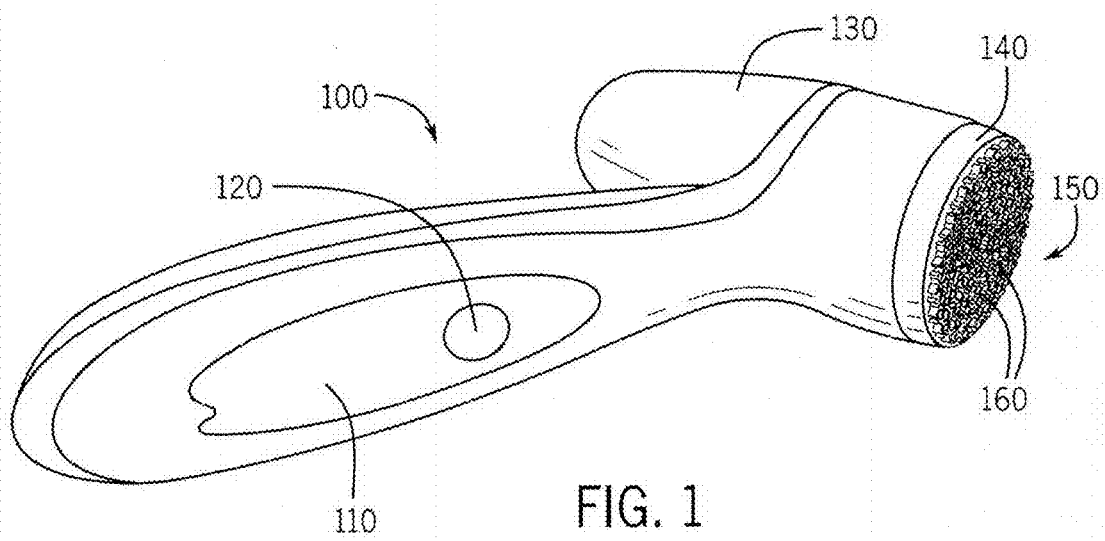
FIG. 1 depicts a pictorial view of a prior art handheld cleansing device and the skin contact surfaces that are driven by at least one motion-generating sub-assembly (here providing oscillation to at least one cleansing surface) contained in the head portion of the device

Although the present disclosure provides descriptions of preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

As used herein, the term "cleansing device" or "device" means a device useful for cleansing the skin of a mammal, for example a person, the device including at least a handle; an electrical motor disposed within the handle and attached to at least one actuator, the actuator situated outside the handle, the motor and at least one actuator or motion source adapted to apply an oscillating movement, for example at a frequency of about 5 Hz to 30 Hz; and a cleansing head attached to the at least one actuator, which serves as a motion source to apply oscillating movement to one or more cleansing head sections.

As used herein, the term "cleansing head" means an article having a first major surface and second major surface, wherein the first major surface has a plurality of cleansing features arranged thereon and the second surface is adapted to be affixed at least to the actuator/motion source of a cleansing device. In some embodiments, the cleansing head includes two or more discrete cleansing head sections, each section including a plurality of cleansing features. In some such embodiments, one or more cleansing head sections are attached to the handle with the second major surface being generally opposite the first major surface and interfacing with the actuator such that at least one cleansing head section is attached to be moved by an actuator. In some embodiments the cleansing head first major surface is substantially planar. In other embodiments, the cleansing head has a curvilinear or arcuate shape, including in some embodiments a hemispherical shape. In some embodiments the cleansing head is generally symmetrical; in other embodiments, the cleansing head includes one or more asymmetries or asymmetrical contours. In some embodiments, the cleansing head includes multiple arcuate shapes.

As used herein, the term "TENS" means Transcutaneous Electrical Nerve Stimulation and refers to the use of various waveforms which may be applied to skin and which have been approved for aesthetic or other human use by the U.S. Food and Drug Administration (FDA).

As used herein, the term "cleansing motion" means the motion delivered by the handheld device to effect the movement of a first cleansing head section relative to a second, adjacent cleansing head section, as measured at two adjacent points, such as two points on opposed sided of their adjacent edges. In one embodiment it is an oscillating movement. The motion may be delivered to only one cleansing head section and not to a stationary adjacent cleansing head section. Alternatively, the adjacent stationary cleansing head section is also oscillating, leading to a total displacement motion that is a result of the combined movement of the sections. Cleansing motion also includes motion delivered to make at least one cleansing head section rotate.

As used herein, the term "handle" or "handle portion" means the portion of the cleansing device that fits in an average human grip in a manner that enables a user to urge the cleansing head of the device toward the user's face, and manipulate the device to slide the cleansing head across the facial surface. The handle further includes the motor and associated wiring, supports, and power input to facilitate the application of electrical power to the motor via DC or AC/DC. In some embodiments, the handle includes a switch for switching the electrical power to the motor or device control module on and off. In some embodiments the handle includes additional controls.

As used herein, the term "electrical motor means a device powered by electricity for generating motion, whether rotary, reciprocal, orbital or otherwise that can be coupled directly or indirectly to a cleansing head or cleansing head section to cause it to move as described herein. It also means a motor that receives motion and can act as a generator for electrical energy derived from the received motion. Such a motor may be a stepper motor or a DC or analog or rotating motor.

As used herein, the term "stepper" or "stepper motor" means a motor controlled by position signals that can be actuated in arc motion increments, e.g. 0.9 or 1.8 degrees, to provide a defined amount of arcuate or rotational motion at an output shaft. Typically, a stepper motor has toothed electromagnets arranged around a central gear or rotor to define position. Alternatively, by applying motion to a shaft to move a rotor with multiple magnets, current can be generated at (induced in) coils of the stepper motor adjacent the moving magnets.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Intended properties include, solely by way of nonlimiting examples thereof, elasticity, modulus, hardness, and shape; intended positions include position of a first cleansing feature relative to a second cleansing feature. Where modified by the term "substantially" the claims appended hereto include equivalents to these types and amounts of materials.

Cleansing Device and Overview of TENS Attachment (FIGS. 1-3A)

Disclosed herein is a cleansing device for cleansing the skin of a mammal, for example a person, the device including at least a handle; an electrical motor disposed within the handle and attached to an actuator, said motor and actuator adapted to be a motion source, i.e., to apply movement to a cleansing head. In one embodiment, the motor and actuator apply an oscillating movement at a frequency of about 5 Hz to 30 Hz to a least a portion of a cleansing head. A cleansing head may have a first major surface and second major surface, with the first major surface comprising a plurality of elastomeric cleansing features, the cleansing features extending away from the first surface. In one embodiment, the cleansing head is partitioned into two or more cleansing head sections, and the actuator/motion source is attached to the second major surface of the cleansing head to apply oscillating movement to one or more cleansing head sections, resulting in a total displacement between head sections per oscillation of about 0.5 mm to 8 mm.

FIG. 1 is a pictorial view of one exemplary embodiment of a cleansing device known in the art. Cleansing device 100 is shown in FIG. 1, wherein device 100 includes handle portion 110, on/off switch 120, and mounting portion 130 that positions and supports cleansing head 140. Cleansing head 140 has cleansing surface 150, which includes multiple elastomeric cleansing features 160. In various embodiments, handle portion 110 includes a motor (not shown) that actuates a selected motion of cleansing head 140 or a section thereof. Cleansing head 140 second major surface (not shown) is attached to an actuator, in one embodiment a moving hub or other motion source (not shown in FIG. 1) of the mounting portion 130 at its interface to the cleansing head 140, in a manner that facilitates the actuation of an oscillatory movement of a portion of the cleansing head. In one embodiment, the oscillation is rotary motion of the hub/motion source back and forth over an arc of a number of degrees, such as 5, 10, 15, 20, 25, 30, 35, 40 45, 50 or more degrees. In one embodiment, the hub/motion source provides arcuate motion, oscillating between the ends of an arc covering between 5 and 90 degrees. In another embodiment, the hub may supply rotating motion. The device 100 preferably has a rechargeable battery inside handle portion 110. The battery device provides electrical energy to the motor and to a control module that actuates the hub/motion source and thus movement of cleansing head 140 or one or more sections thereof.

The following are representative dimensions of the cleansing device. In the embodiment shown, height H of the device is between about 140 mm to 200 mm, or about 170 mm to 180 mm. Width W of the device is about 30 mm to 70 mm, or about 40 mm to 60 mm. Depth D of the device is about 50 mm to 120 mm, or about 70 mm to 100 mm.

Various other configurational embodiments of the cleansing device 100 are possible, as long as the cleansing head is removable and its removal leaves a motion source accessible.

The movement of the cleansing head sections is generated by at least one motor coupled to actuate movement by the attachment of a cleansing head section to the hub/motion source or actuator. It will be appreciated that in some embodiments, the cleansing head housing is attached to the handle, while one or more cleansing head sections are attached to one or more actuators. In some embodiments, one or more cleansing head sections are attached to one or more actuators to provide an oscillatory movement, while one or more additional cleansing head sections are attached to the handle to provide one or more stationary cleansing head sections. In other embodiments one or more actuators provide counter-oscillatory movement of two or more cleansing head sections.

Cleansing head 140 is removable from cleansing device 100, for cleaning and to provide access to an actuator mechanism, e.g., a hub/motion source (not shown in FIG. 1; see FIG. 10a at 1010) that delivers motion to an attached cleansing head section. Additional details of the cleansing head and the actuator mechanism (in various embodiments) can be found in U.S. Patent Application Publication 20160045081 for Device and Method for Cleansing and Treating Skin, Ser. No 14/825316 and Device And Method For Cleansing And Treating Skin in PCT Application No. PCT/US2016/046738, which are incorporated herein by reference.

The handle portion of the device 100 houses the motor, which is either directly powered by AC/DC power or is battery powered. The handle further includes associated wiring, supports, and power input via a supply circuit to facilitate the application of electrical power to the motor via DC or AC/DC. If externally powered, a cord is provided that allows a user to plug the cleansing device into a standard wall socket (120V, 60 Hz in North America for example) and converts the power to DC. If the cleansing device is battery powered, a recharging cord is removably attached to the device and the charging cord plugs into a standard wall socket for recharging depleted batteries. In some embodiments where the device is battery powered and rechargeable, a charge level sensor is coupled to a display visible to a user, wherein the user is alerted to the status of the remaining battery power. In some embodiments, the handle 110 includes a switch 120, available to a user for switching the electrical power to the motor on and off.

In some embodiments, the cleansing device further houses a timer (typically based on a timer circuit or programmed microprocessor) that beeps, vibrates, or otherwise notifies the user that a particular increment of time has passed. For example, a timer algorithm that causes a beeping signal to sound every 15 seconds, or every 30 seconds, or some other interval when the cleansing device is turned "on" is useful to alert the user that he or she should start addressing a different area of the skin. The timer interval is usefully employed in conjunction with an automatic "off" switch housed internally that shuts the device off after a certain number of timed intervals. For example, in some embodiments, a timer routine is implemented that vibrates every 15 seconds, and after four 15 second intervals (during which the timer vibrates three times), the device automatically shuts off. In some embodiments, the user can select (via a control situated on the handle) a skin cleansing program, wherein the timer and automatic shut off are programmed for facial cleansing, gentle facial cleansing, foot cleansing, and the like.

The handle portion 110 fits in an average human grip in a manner that enables a user to comfortably place the cleansing head 140 cleaning surface 150 in contact with the user's face with some applied pressure, and manipulate the device to slide the cleansing features 160 across the facial surface.

Figure 2:
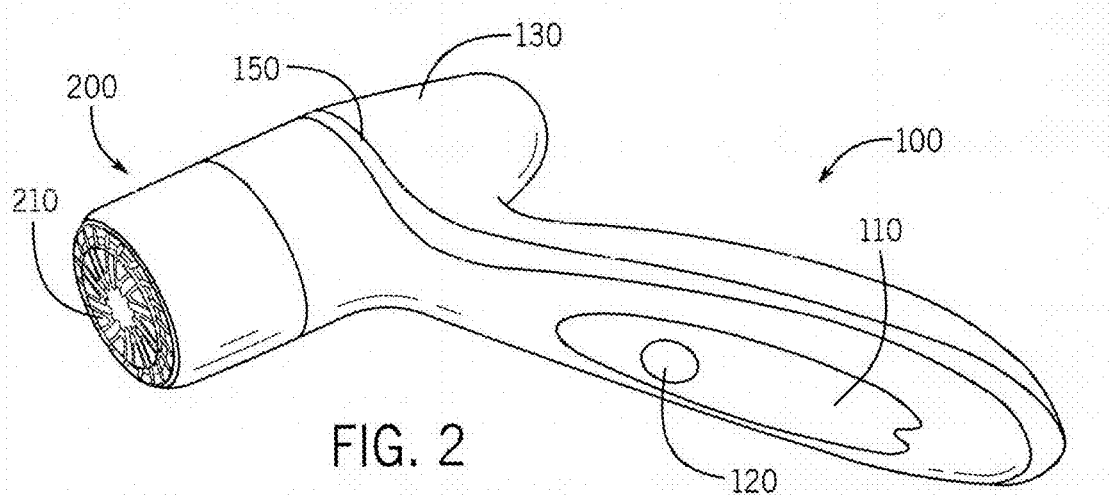
FIG. 2 depicts a pictorial view of a handheld cleansing device in which a portion of the head with the skin contact surfaces that are driven to oscillate by the motion-generating sub-assembly has been replaced by an attachment that receives the motion generated and delivers TENS treatment current through conductive skin contact surfaces.

FIG. 2 is a pictorial view of one exemplary embodiment of a cleansing device 100 of FIG. 1 in which the cleansing head 140 has been removed and replaced by a TENS attachment 200 that includes a skin contact surface 210 with electrodes. As can be seen, the device 100 remains the same, as to the handle portion 110, on/off switch 120, and mounting portion 130, except that the latter now positions and supports the TENS attachment 200 with its skin contact surface 210.

Head Assembly (FIGS. 3A-3D)

Figure 3A:
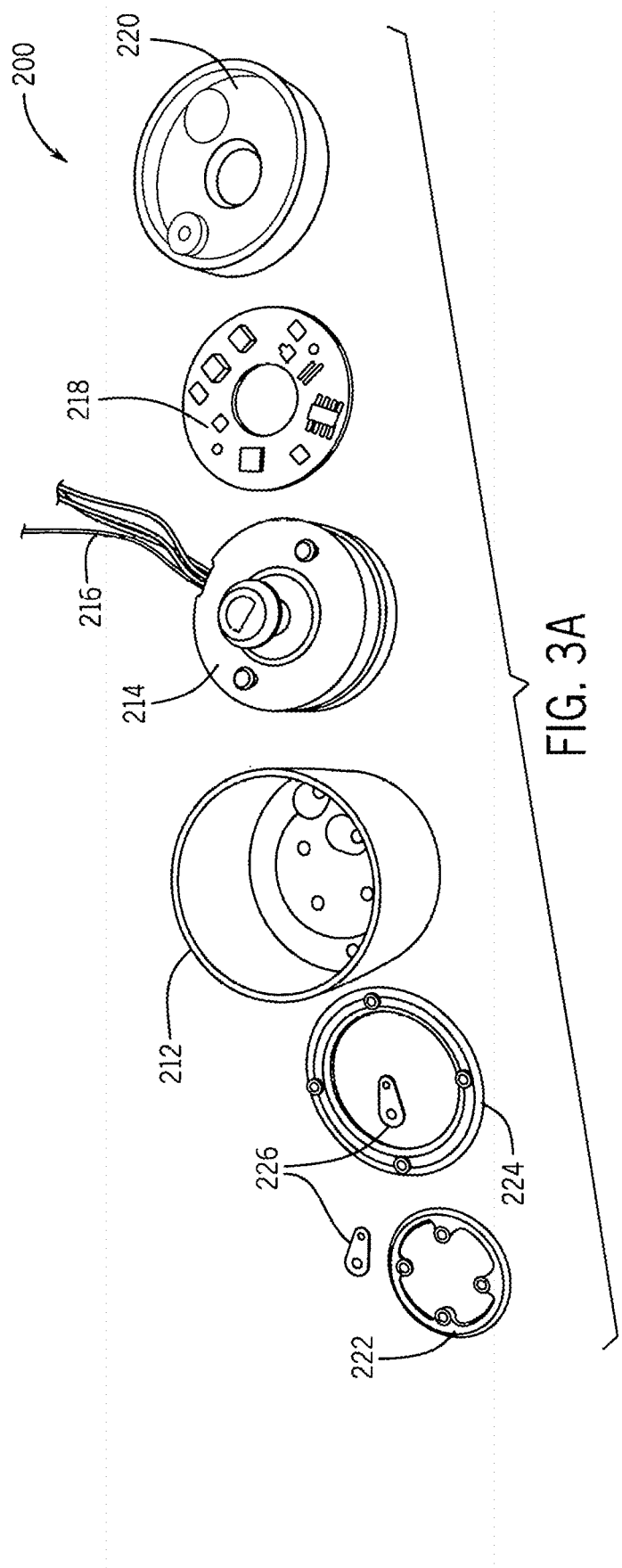
FIG. 3A shows in pictorial form an overview of the major parts and subassemblies of the TENS delivery attachment of FIG. 2, unassembled.

FIG. 3A is a pictorial view of the unassembled components of the TENS attachment 200. These components include the head cover or housing 212, a motor/generator and coupling assembly 214 with output wires 216, a printed circuit board 218 for the circuitry to be described below, and a motor adapter 220 to aid secure mounting of the motor/generator and coupling assembly 214 on the mounting portion 130 after removal of the cleansing head 140. FIG. 3A shows in addition, center head contact or electrode 222, the outer head contact or electrode 224 and two wire solder lugs 226 usable to connect to the center and outer head contacts or electrodes 222, 224.

Figure 3B:
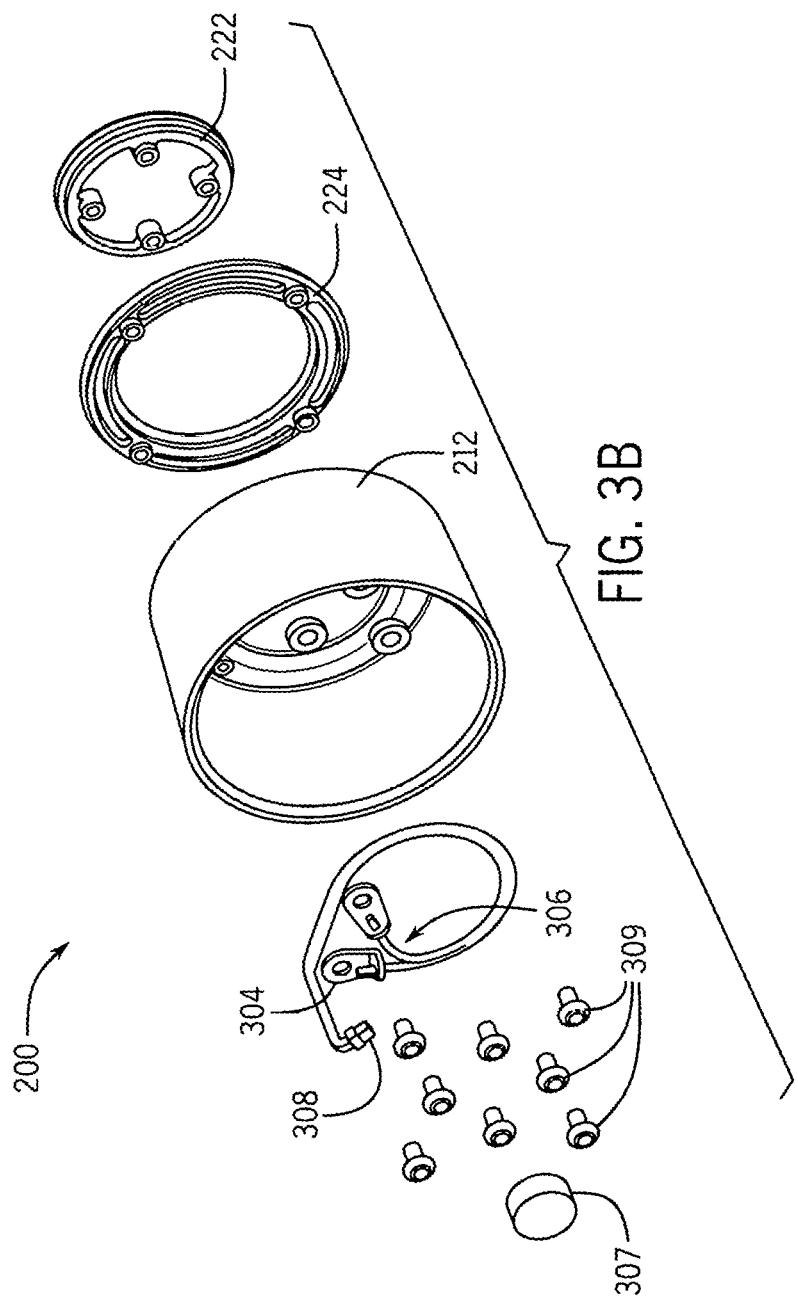
FIGS. 3B-3D show, respectively: an exploded view of the parts of the head cover or housing assembly for the TENS attachment; a view looking inside the head cover; and a view showing assembly of the motor and circuitry assembly into the head cover.

FIG. 3B shows an exploded view of the parts of one embodiment of the head cover subassembly for TENS attachment 200. Moving generally from left to right in FIG. 3B, the parts include a head spring 307, various connector screws 309, a connector plug 308 attachable to the TENS waveform generating circuit described below, and a pair of solder lugs 304 connected to the outer head contact wire 305 and inner head contact wire 306. FIG. 3B further shows head cover or housing 212, center head contact or electrode 222, and outer head contact or electrode 224

Figure 3C:
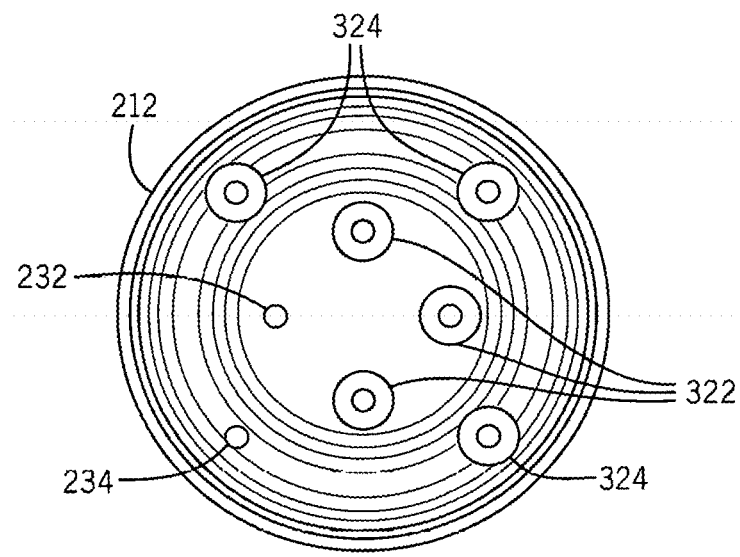

FIG. 3C shows a view looking inside the head cover or housing 212; with the wire attachment points 232, 234 for the center head contact or electrode 222, and outer head contact or electrode 224. Also shown are three screw attachment points 322, 324 on the top surface of head cover 212 for each of the center head contact or electrode 222, and outer head contact or electrode 224

Figure 3D:
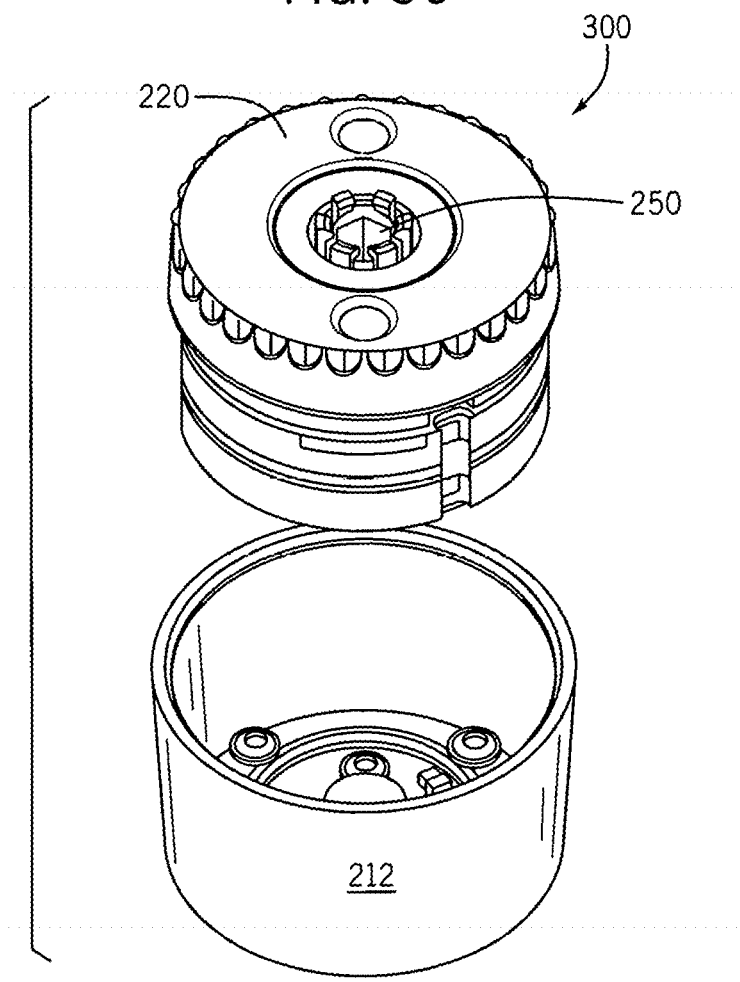

FIG. 3D shows a view of assembly of the motor and circuitry assembly 300 into the head cover or housing 212. Here the motor adapter 220 and motor coupling 250 are also shown. The motor in one embodiment is a bipolar stepper motor (see FIG. 9 at 900), specifically a pancake stepper motor that can receive arcuate or rotary motion at its rotor and generate current when the magnets in a circular array on the rotor are moved past an array of coils that surround the rotor.

A bipolar stepper motor is typically used for positioning applications by a controller circuit delivering pulses of current to two or more pairs of coils that are outside of a circular set of permanent magnets that make up a rotor. The pulses cause the rotor to move from one angular position to another. This same configuration can be used to generate current by rotating the rotor, so that the permanent magnets induce current in the surrounding coils. Each time a magnet passes a coil, a pulse of current is induced. If a rotor magnet is spun past multiple coils, a string of pulses is generated, one from each coil/magnet interaction. In the present situation with a motion source that delivers oscillation in the form of rotary motion of the hub/motion source back and forth over an arc of a number of degrees, such as 5, 10 15, 20, 25, 30, 35, 40 45, 50 or more degrees, the number of pulses of current induced for a given arc of motion delivered to the rotor of a stepper motor depends on the number of times a magnet on the rotor passes a coil of a stepper motor as the rotor travels over an arc of a specified number of degrees. In one embodiment, the motion source delivers motion of approximately 44 degrees of arc in one direction and reverses to move back over the same arc of 44 degrees in the opposite direction.

A stepper motor may be defined by the number of degrees of arc in one of its steps. For example, a motor may have a 3.6° step (e.g., 100 steps to a full rotation), or have a 1.8° or 0.9° step or other arc amount per step. For the stepper used in one embodiment, the approximate number of pulses generated by motion of approximately 44 degrees of arc in one direction for each of these is as follows 3.6° yields~3 pulses
1.8° yields~6 pulses
0.9° yields~12 pulses For purposes of the present application, the exact number of pulses delivered from an arc motion is not critical, as long as it is not too few in total energy supplied for downstream circuits. More pulses provided allows a smoother DC output to be derived from a pulse train developed at the output of stepper motor 900 from its receiving the continuing oscillation (at a frequency in the range from about 5 Hz to about 30 Hz) over 44 degrees of arc of the hub/motion source 1010 of the handheld device 100, using the power generator circuit described next.

Figure 4:
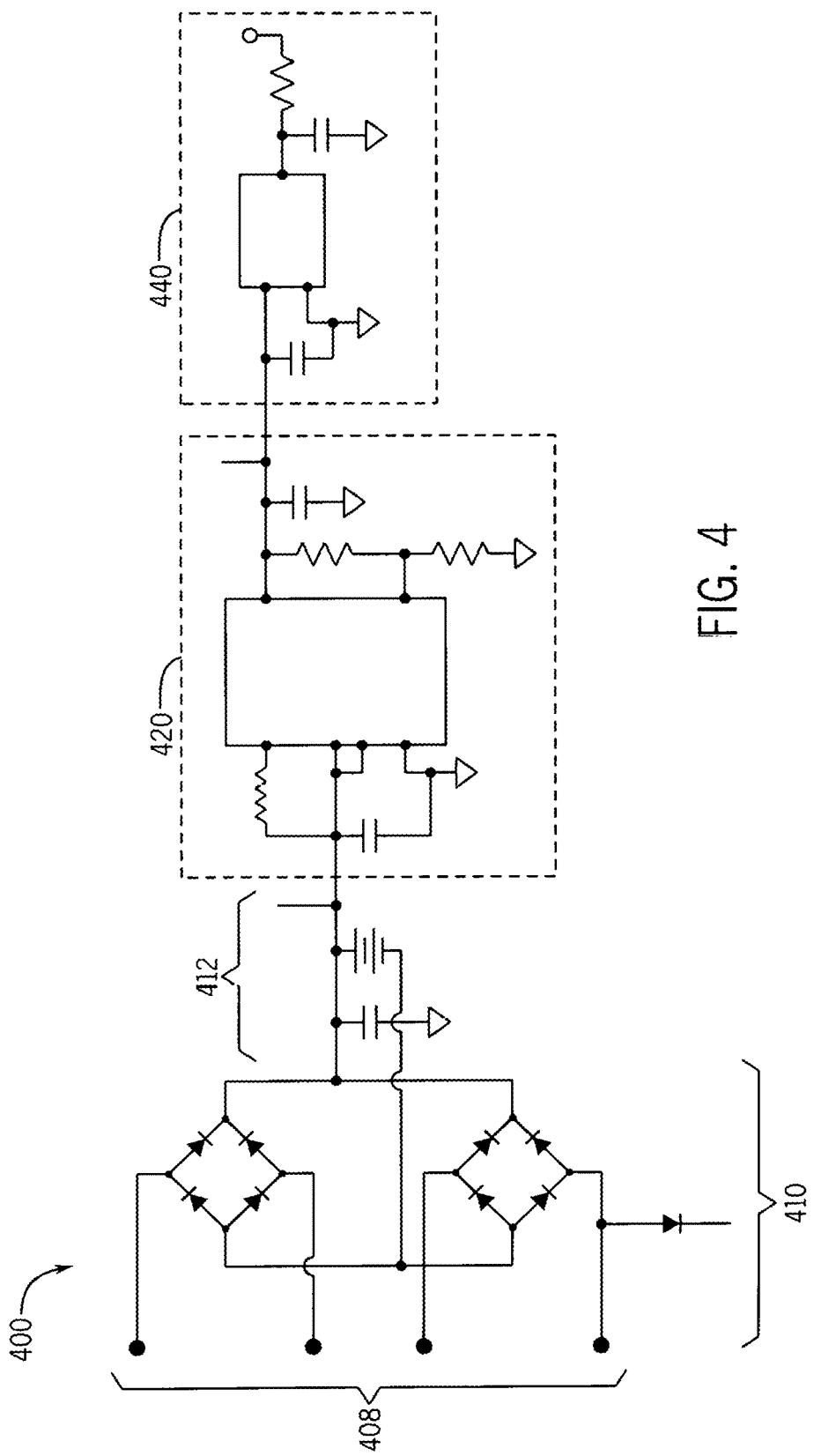
FIG. 4 shows a schematic circuit diagram of the power generating circuit subassembly of the TENS delivery attachment shown in FIG. 2.
Figure 6:
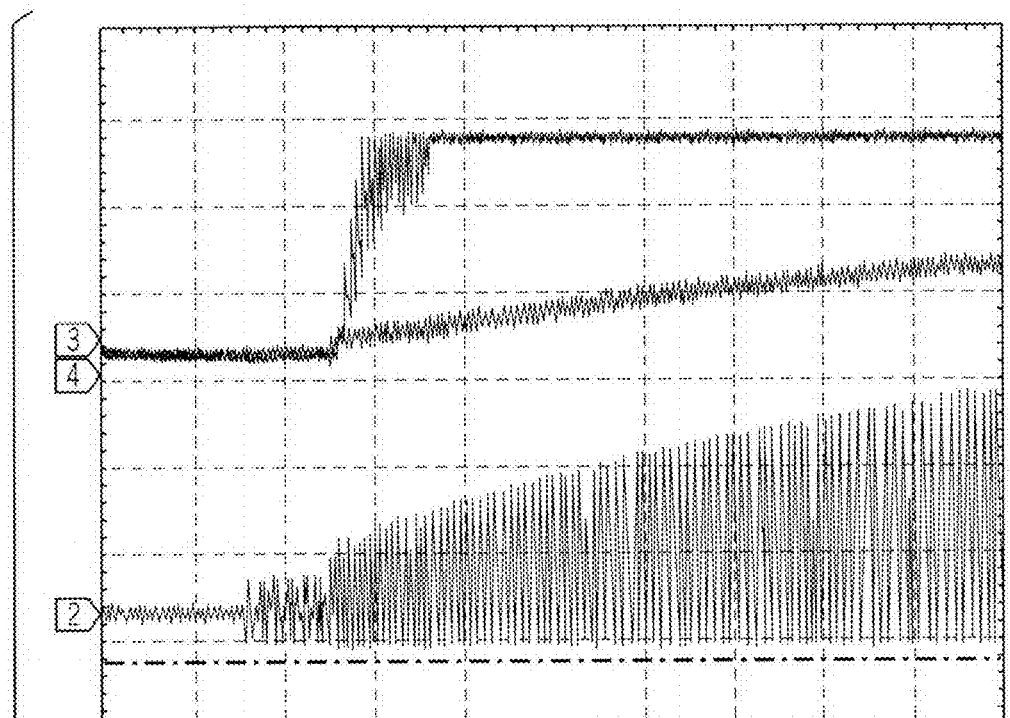
FIG. 6 shows various voltage waveforms observed from the circuit subassemblies of FIG. 4.
Figure 6:
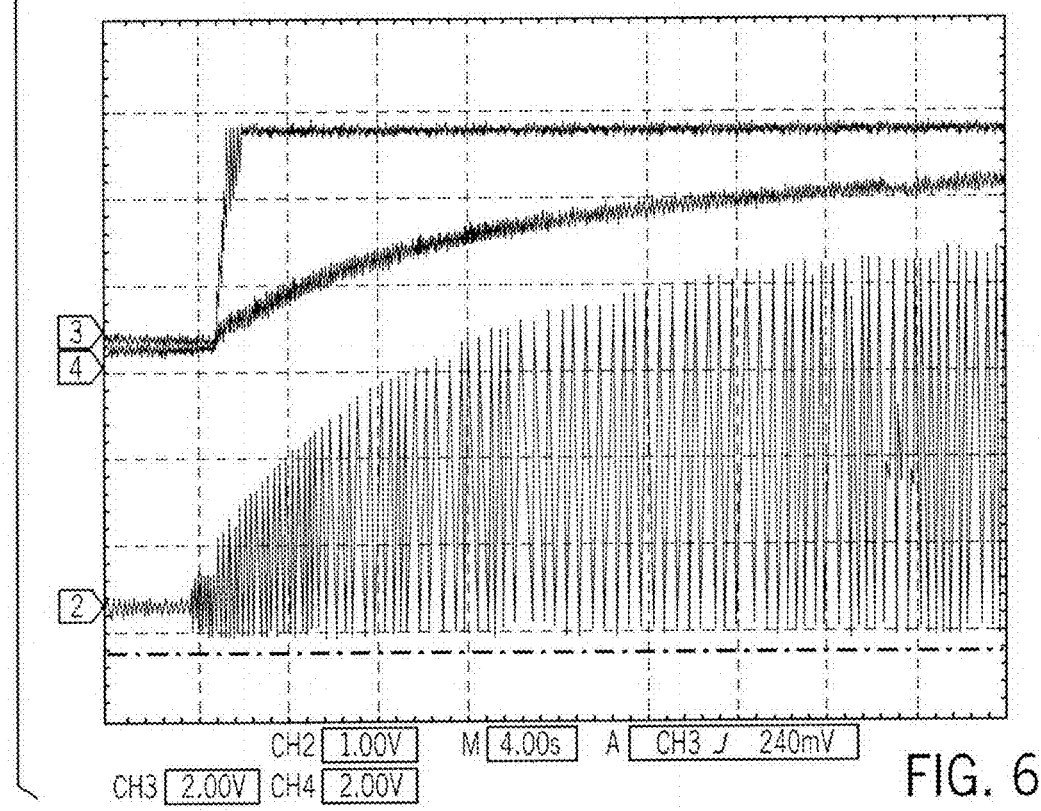

Power Generator Electronics Subassembly (FIGS. 4, 6)

The attachment 200 has in one embodiment a power generator circuit 400 as shown in FIG. 4. To the left in FIG. 4 are two full wave bridge rectifier circuits 410 receiving at their four input points 408 at the left of FIG. 4 the AC output of a bipolar stepper motor (not shown in FIG. 4) for rectification. Moving to the right in FIG. 4, power generator circuit 400 has a circuit 412 with capacitors, to build up charge from the rectified AC. The output voltage of the capacitors is connected to an input of a Boost Supply circuit 420, which has as its central component a step-up converter, e.g. Texas Instruments TLV61220. This Boost Supply circuit 420 in turn has its output connected to an input of a Logic Supply circuit 440. The circuit 412 supplies a relatively low voltage, e.g., about 1 to 2 volts to the Boost Supply circuit 420, which provides an output in one embodiment of about 5 volts to the Logic Supply circuit 440. Logic Supply circuit 440, which has as its central component an LDO (low-dropout) regulator, e.g. Texas Instruments TPS71530, which provides a stable, clean output in one embodiment of about 3 volts to provide power to a microprocessor or other logic circuit (see FIG. 5).

FIG. 6 shows the waveforms observed from the circuit subassemblies of FIG. 4. The bottom-most waveform in each screenshot or graph is the raw high frequency AC signal that is the output from the windings of the stepper motor which, through the mechanical connection to the mechanical motion source of the cleansing device 100, is driven as a generator. The next trace above the bottom-most waveform in each screenshot is the rectified voltage from the stepper motor phases. The top trace is the approximately 5 V output of Boost Supply circuit 420 (boost regulator), which is desired to drive other circuitry, including the Logic Supply circuit 440. The 5V output is then conditioned in the Logic Supply circuit 440 to make it suitable as a supply current to a low-power microprocessor for TENS signal generation timing. The left side screenshot in FIG. 6 (1-second per division) is a snapshot of the initial voltage rise (green) as the 5 volt boost supply becomes operational (violet). In this instance, this is seen to take about ~2 seconds. The screenshot on the right (4-seconds per division) shows the increasing (next trace above the bottom-most waveform) rectified voltage rise as the capacitor circuit charges and stabilizes (about 5 seconds in this instance). Depending on motor and component tolerances, the voltage rise times will vary to a degree, but the graphs are a representative example of what is to be expected from a circuit of the general design shown in FIG. 4.

The control system of the cleansing device 100 that allows the user to turn that device on and off at switch 120 initiates action of the motion source 1010 to which the TENS attachment connects. Thus, switch 120 continues as the on/off control also for the TENS output of the TENS attachment 200.

Figure 5:
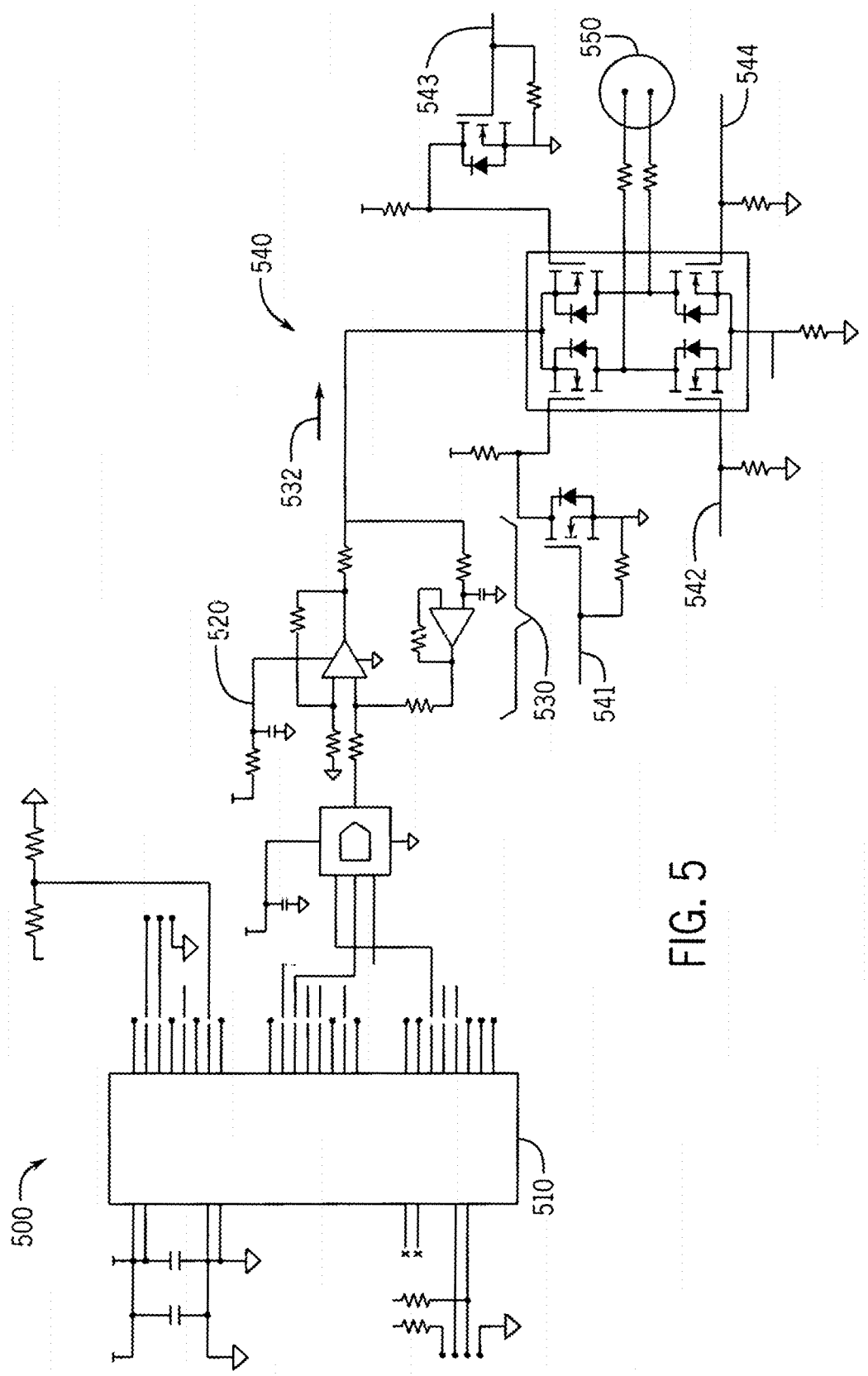
FIG. 5 shows a schematic circuit diagram of the TENS waveform generating circuit subassembly of the TENS delivery attachment shown in FIG. 2.
Figure 7:
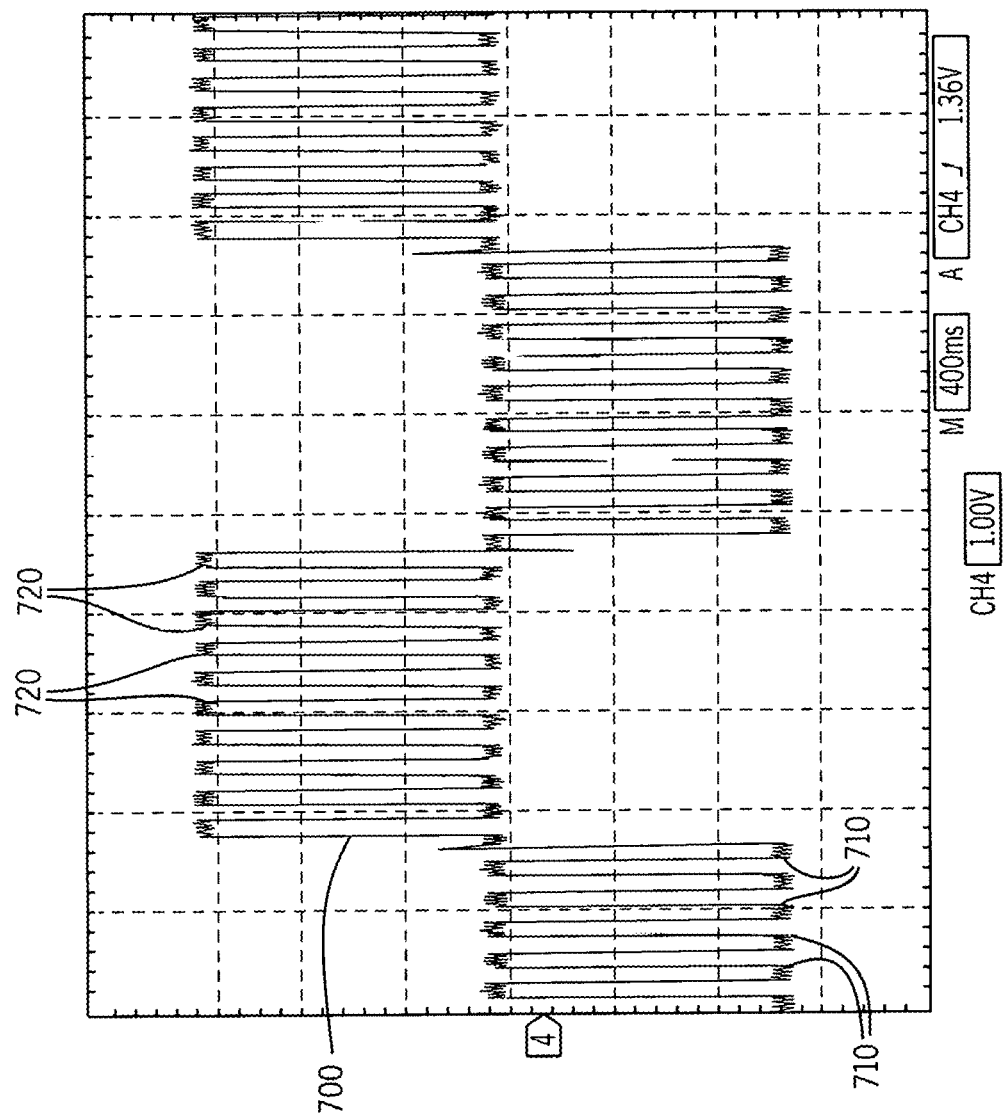
FIG. 7 shows the TENS output waveform observed from the circuit subassemblies of FIGS. 4 and 5.

TENS Waveform Generation Electronics Subassembly (FIGS. 5, 7)

FIG. 5 shows a schematic circuit diagram 500 of the TENS waveform generating circuit subassembly of the TENS delivery attachment shown in FIG. 2. At the left of FIG. 5 is an ultra-low power microprocessor 510 for signal generation timing, such as TEXAS Instruments MSP430. The microprocessor is configurable by programming or other means to determine one or more parameters of a TENS signal, to give the signal a waveform suitable for aesthetic TENS treatment, i.e., a waveform that the US FDA will view as acceptable in a 510k application pointing to one or more aesthetic TENS waveforms of a predicate device previously approved in a 510k application. Certain outputs of the microprocessor 510 are supplied to a digital to analog convertor (DAC) 520 and other to a precision current source circuit 530 based on two op amps. The current 532 from the precision current source circuit 530 is connected to a full bridge output circuit 540 for single ended signal phase reversal, i.e., it controls the polarity of the TENS output waveform, based on signals supplied by the microprocessor 510 at inputs 541, 542, 543, 544.

These various circuits permit a TENS output signal with the desired waveform, power level and the changing polarity as accepted by the FDA for aesthetic TENS application to be delivered at the output wire pair 550. Filings with the FDA for the Rejuvenique Model #RJV10 from Salton, Inc.; Facial Toning System from Face Master; Nutritone from Isomera; and Trinity from Carol Cole—NuFace, mentioned above, show several FDA-approved aesthetic TENS waveforms, which may be used substantially identically or in one or more variant forms in one or more embodiments of the present device. More specifically, the microprocessor 510 provides at four input points 541-544 to full bridge output circuit 540 signals that control and thus allow the specification of the timing, pulse duration and other parameters of the output waveform and its polarity.

FIG. 7 shows a sample waveform output 700 from the circuitry of FIG. 5. As can be seen, the output consists of a sequence of pulses 710 of one polarity, followed by a similar sequence of pulses 720 of opposite polarity. This is a known aesthetic TENS waveform, approved for aesthetic TENS use by the FDA.

Based on tests of devices approved for aesthetic TENS in FDA filings, it appears that currents in the range from about 0.003 mA to about 0.700 mA (depending on the load resistance) and voltages from about 0.1 to about 6.0 V (again depending on the load resistance) are suitable for aesthetic TENS. The circuitry of FIG. 5 is programmable by programming the microprocessor 510. Accordingly, voltage and current levels and waveforms suitable for FDA approved TENS that are not specifically aesthetic TENS waveforms may also be produced by the circuitry of FIG. 5. Waveforms found to be therapeutic for skin by existing or future research may thus be implemented in the present device by suitable programming of microprocessor 510.

TENS Attachment Housing and Skin Contact Electrodes; Coupling to Handheld Base (FIGS. 8A-8D)

Figure 8A:
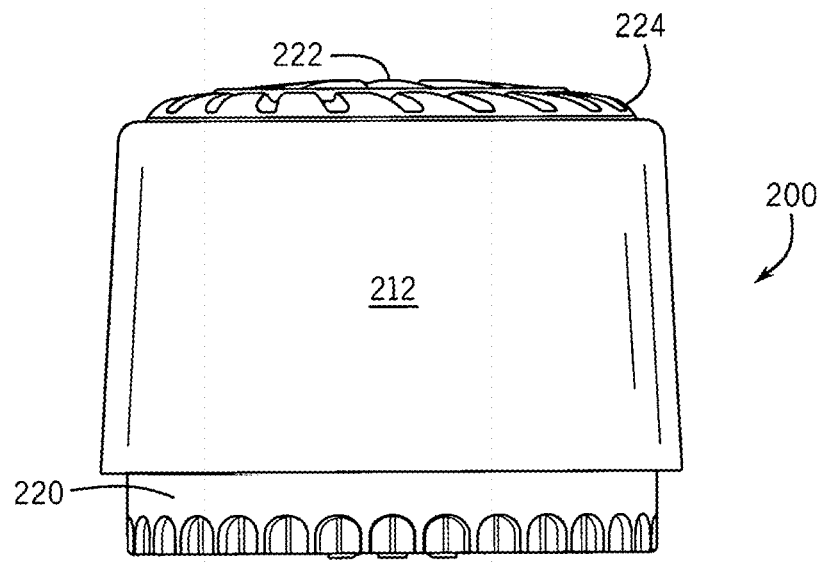
FIGS. 8A-8D are side, top and orthogonal top and bottom views of the TENS attachment disclosed herein.
Figure 8B:
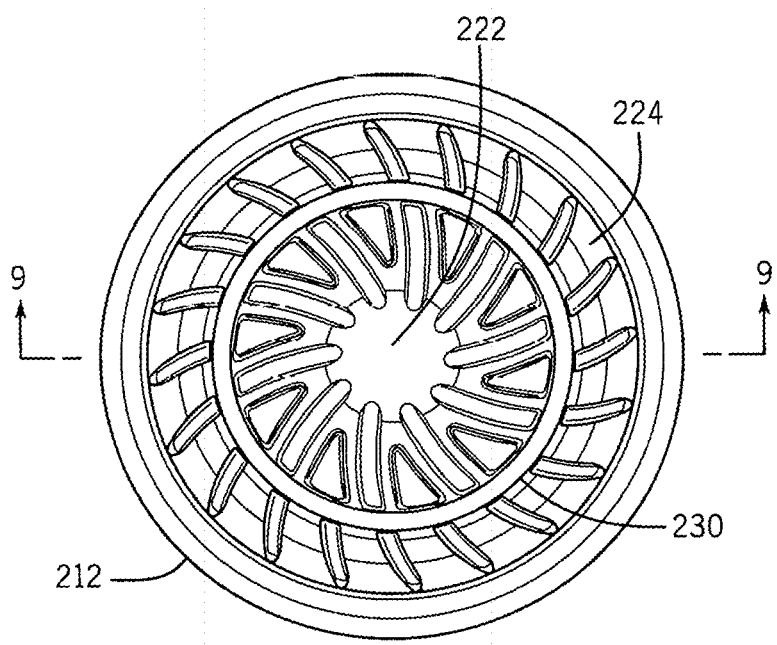

FIGS. 8A-8D show additional aspects of the housing 212 for the TENS attachment and the TENS output electrodes. FIG. 8A show a side view of the TENS attachment 200 with housing 212 and motor adapter 220. At the top of FIG. 8A the center head contact 222 and the outer head contact 224 are visible. These are the electrode pair that, in the embodiment shown, contacts the skin and, when both electrodes are in skin contact, delivers to the contacted skin between them current with the TENS waveform. FIG. 8B shows a top view of the two electrodes/contacts 222, 224 mounted on the housing 212 of the TENS attachment. The two electrodes are separated by an insulator 230. The housing 212 is configured to support the first and second output electrodes in a generally planar configuration for skin contact. The planar configuration may have a gentle convex curvature as shown in FIG. 8A. As can be seen, the two electrodes/contacts 222, 224 may have a shallow surface pattern. This pattern may be selected primarily for visual appeal or may also have shallow channels between wider flat areas that can assist in distributing lotion-type substances that may be used to improve conductivity with the skin, reduce friction that might impair user comfort or provide other skin benefits. It has been found that the use of conductive lotions between the skin-contacting electrodes and the skin may improve user comfort, because it assists in dispersing the current flow evenly and over a larger skin area. This reduces the chance of the current density at any point on the contacted skin being so high that it produces an unpleasant sensation.

Figure 8C:
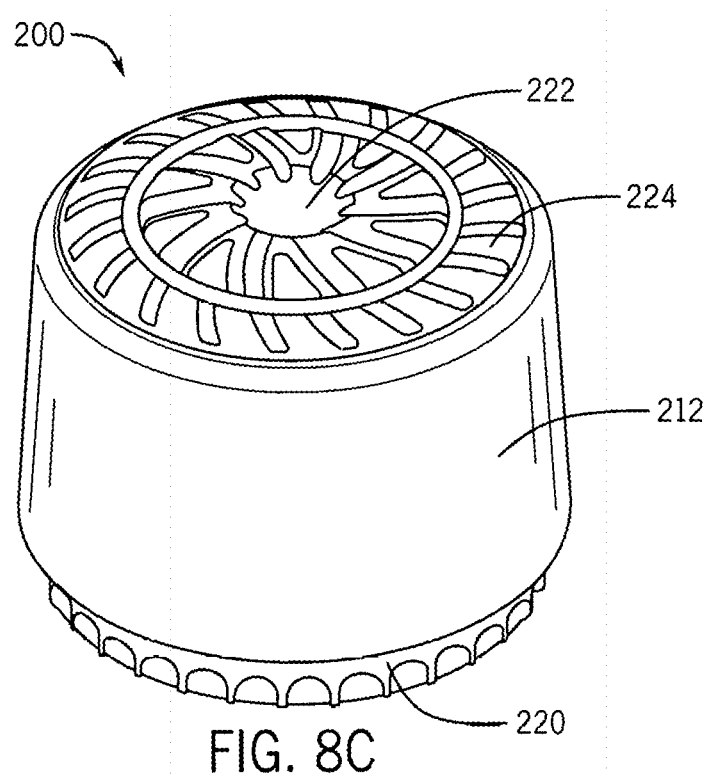
Figure 8D:
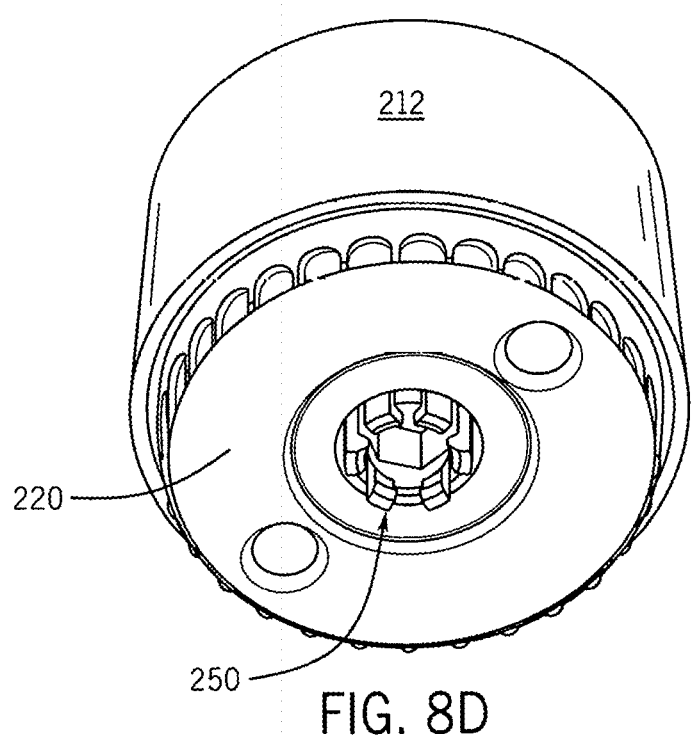

FIG. 8C is an orthogonal view of the TENS attachment 200, again showing the two electrodes/contacts 222, 224 mounted on the housing 212. Also seen here is the motor adapter 220 at the base of the TENS attachment 200. FIG. 8D is an orthogonal view of the bottom of the TENS attachment 200, again showing motor adapter 220 at the base. Here the motor coupling 250 is also seen. This is a socket with multiple arms that clip onto a hub/motion source 1010 (see FIG. 10A). In one embodiment the hub 1010 is a hexagonal hub and motor coupling 250 is mated to it to provide good transfer of motion to the stepper motor of the embodiment shown.

Figure 9:
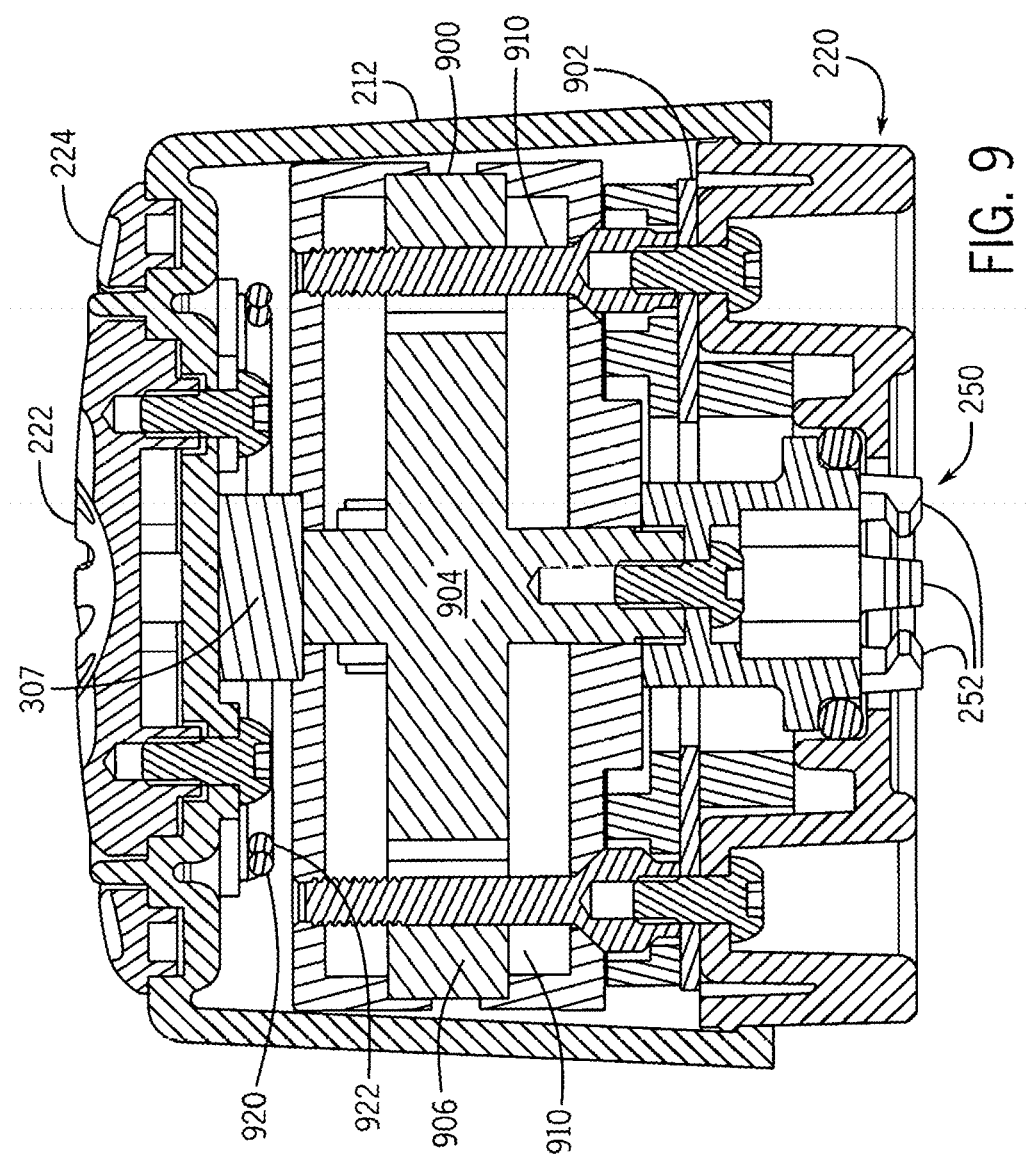
FIG. 9 is a cross-sectional view (taken at A-A in FIG. 8B) of the TENS attachment disclosed herein, showing among other parts the motor coupling to the handheld device, the stepper motor receiving the coupled-to motion and the skin contacts acting as electrodes for the TENS output signal.

FIG. 9 shows in cross-section and in greater detail the interior of the TENS attachment 200. This includes the head cover or housing 212 and motor adapter 220 and the two electrodes/contacts 222, 224 mounted on the housing 212 as already described. FIG. 9 also shows the bipolar, "pancake" stepper motor 900 with its mounting screws 910 and with the motor printed circuit board 902 fastened to the bottom of the motor 900. Also shown in FIG. 9 are the contact head wire 920 for the outer contact and the head wire 922 for the inner contact. At the center bottom of FIG. 9 is the motor coupling 250, with its multiple clip arms 252 that make the attachment to the hub (hexagonal in one embodiment; not shown in FIG. 9) of the mounting portion 130 that serves as the motion source of the handheld device 100. The motor coupling 250 has multiple arms 252 that grasp the hub/motion source and transfer to the center axis 901 and magnet rotor 904 connected thereto the motion of the motion source. In one embodiment, the motion source provides an arc of motion of about 44 degrees, oscillating between the ends of the 44 degree arc. The magnet rotor 904 is surrounded by an annular array 906 of coils in which motion of the magnets of the rotor 904 induce currents. These currents are AC, roughly sinusoidal and are the inputs to the full wave bridge circuit 410 where the AC signal is rectified.

Figure 10A:
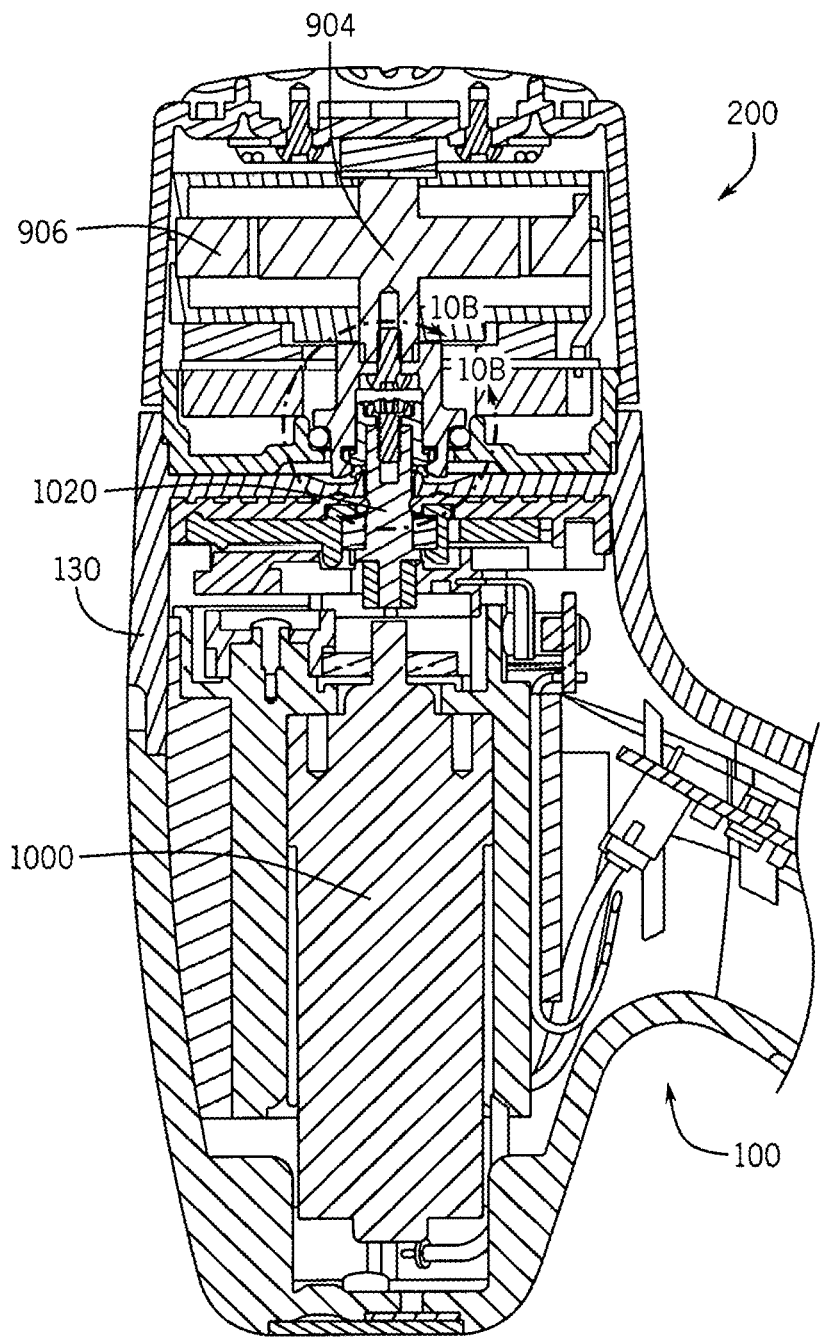
FIG. 10A is a cross-sectional view (taken at A-A in FIG. 8B) of the TENS attachment disclosed herein attached via the motor coupling to the handheld device, showing the motor of the handheld device generating the motion converted into electrical energy in the attachment and showing the TENS attachment motor coupling receiving the coupled-to motion of the motion source and the skin contacts that act as electrodes for the TENS output signal.
Figure 10B:
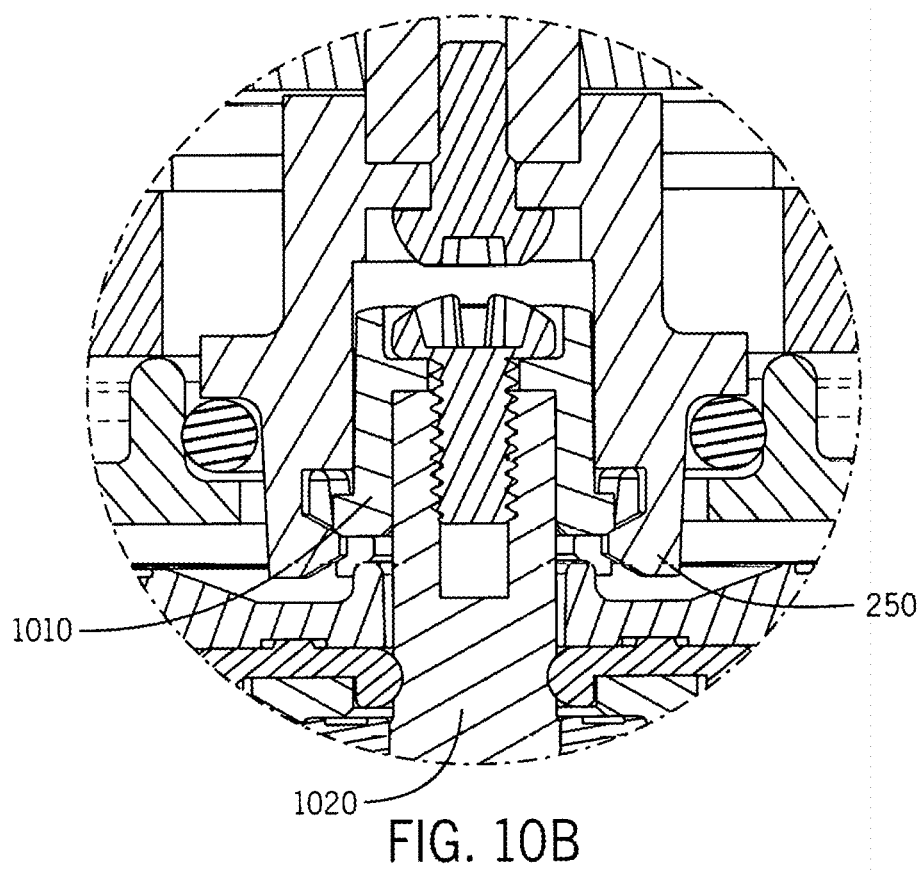
FIG. 10B is a detail view of the circled portion of FIG. 10A.

FIG. 10A shows in cross section a TENS attachment 200 supported on and attached to the mounting portion 130 of the handheld device 100. FIG. 10A also shows the motor 1000 in the handheld device 100 that in the embodiment shown drives the motion source 1010. In one embodiment, this is a DC motor that can be controlled to move in an arcuate pattern, rotating the motor axis 1020 and attached hub/motion source 1010 between the ends of the rotation arc. FIG. 10B shows in greater detail the axis 1020 and hub/motion source 1010 grasped by clip-on, resilient arms 252 of the motor connector 250

Alternative Mechanical Energy Conversion or Connection Modules

In some embodiments the handheld cleansing device and/or the TENS attachment differs from the embodiment described in FIGS. 1-10 above. In particular, the nature of the motion source may involve rotational motion instead of oscillation and/or the mechanical energy conversion module may perform the conversion of mechanical energy (rotating or oscillating) into electrical energy or connection to such energy in a different way. The following chart shows the possible alternatives, whereby oscillating or rotating motion sources can be connected to, and the source of mechanical motion can be converted into, electrical energy.

The double-headed arrows in the chart below denote oscillating motion. Single-headed arrows in the chart below denote rotation in a direction.

|   | Motion source | Connector motion in TENS attachment | Mechanical conversion | Mechanical to electrical conversion |
|---|---|---|---|---|
| 1 | Oscillating ↔ | Oscillating ↔ | n/a | Stepper motor/generator ↔ |
| 2 | Oscillating ↔ | Oscillating ↔ | Oscillating to rotating → | Rotary motor/generator → |
| 3 | Rotating → | Rotating → | Rotating to oscillating ↔ | Stepper motor/generator ↔ |
| 4 | Rotating → | Rotating → | n/a | Rotary motor/generator → |
| 5 | Oscillating or rotating ↔ → | Oscillating or rotating ↔ → | Compression on or distortion of piezo elements | Piezo effect charge generation and capture for current |

Row 1 of the above chart represents the operating principle of the first embodiment described above. An oscillating motion source 1010 causes a connector in a TENS attachment 200 to oscillate. Assuming a sufficient arc of oscillation and using the connector to drive the rotor of a stepper motor with small arc steps, a string of pulses can be generated at the outputs from the stepper motor coils. This string of pulses can be rectified and processed in power boost and logic supply circuitry to provide sufficient electrical current to power a TENS signal generator circuit, capable of producing an aesthetic or other TENS waveform.

Row 2 of the above chart represents a variation of the operating principle of the embodiment described above. An oscillating motion source 1010 causes a connector in a TENS attachment also to oscillate. The oscillation can be converted in a TENS attachment to a rotary motion by a known crank mechanism with a wheel or gear with an offset pin. The rotary motion can be coupled to drive the rotor of a rotating motor generator, which can generate AC current at the outputs from the generator motor coils. This AC current can then be rectified and processed in power boost and logic supply circuitry to provide sufficient electrical current to power a TENS signal generator circuit, capable of producing an aesthetic or other TENS waveform.

Row 3 of the above chart represents a further variation of the operating principle of the embodiment described above. When a rotating motion source is available, it can cause a connector in a TENS attachment also to rotate. The rotation can be coupled to drive the rotor of a rotating motor generator, which can generate AC current at the outputs from the generator motor coils. This AC current can then be rectified and processed in power boost and logic supply circuitry to provide sufficient electrical current to power a TENS signal generator circuit, capable of producing an aesthetic or other TENS waveform.

Figure 12A:
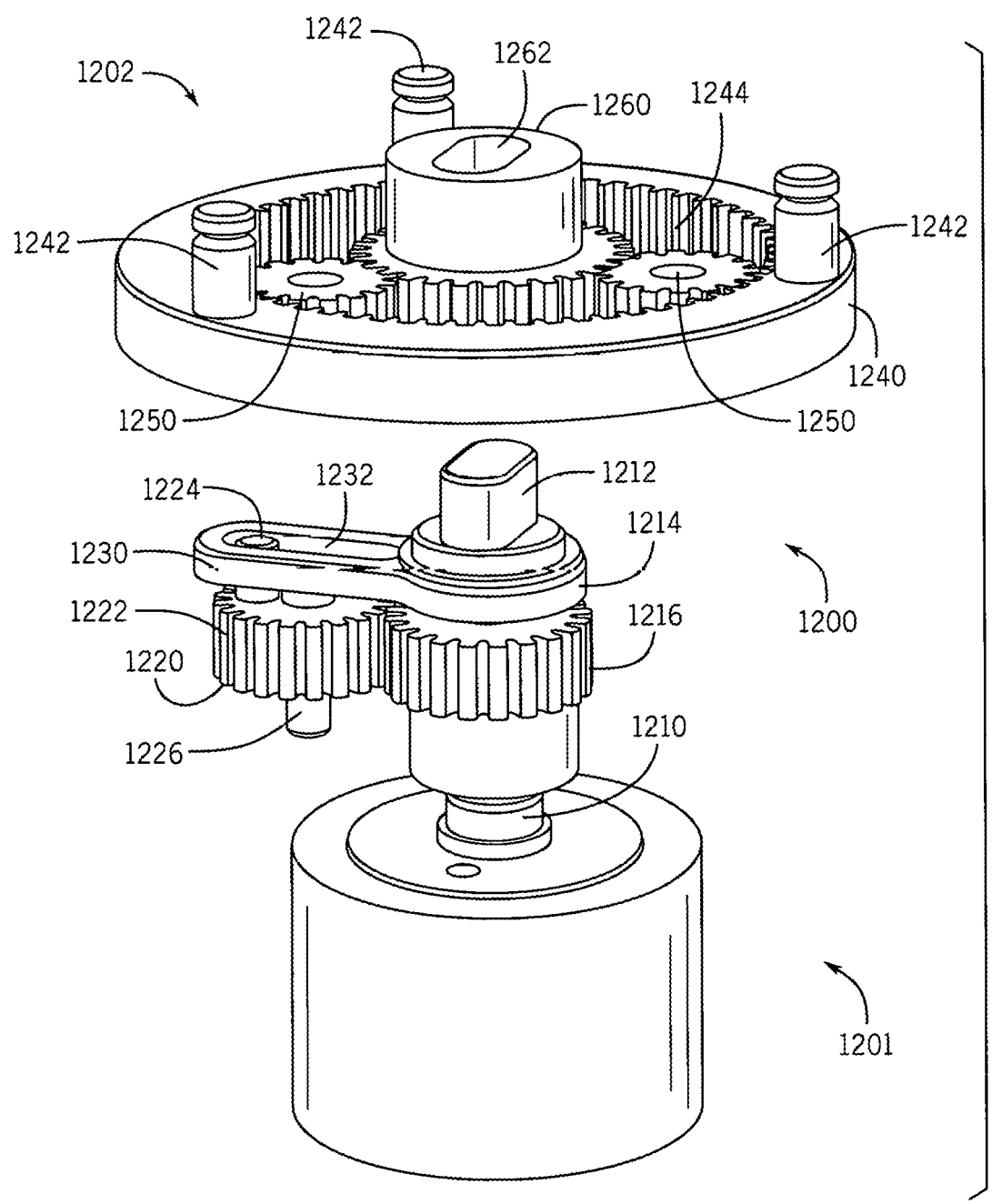
FIGS. 12A-12C show a prior art mechanism for converting rotational motion of a motor into oscillatory motion to provide a motion source for one or more sections of a cleansing head; the mechanism is usable in one or more embodiments of the present device.
Figure 12B:
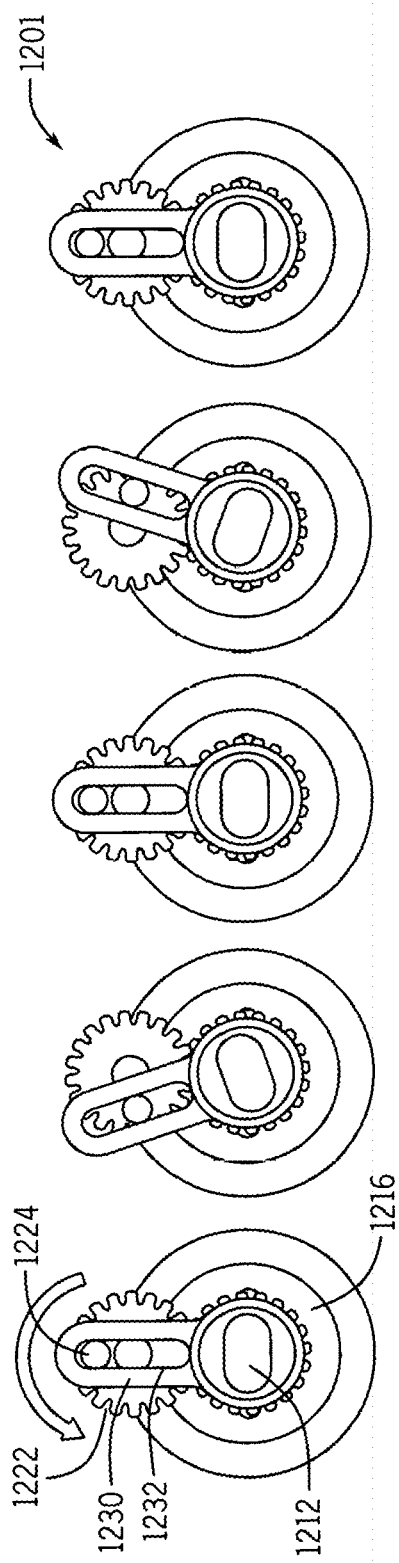
Figure 12C:
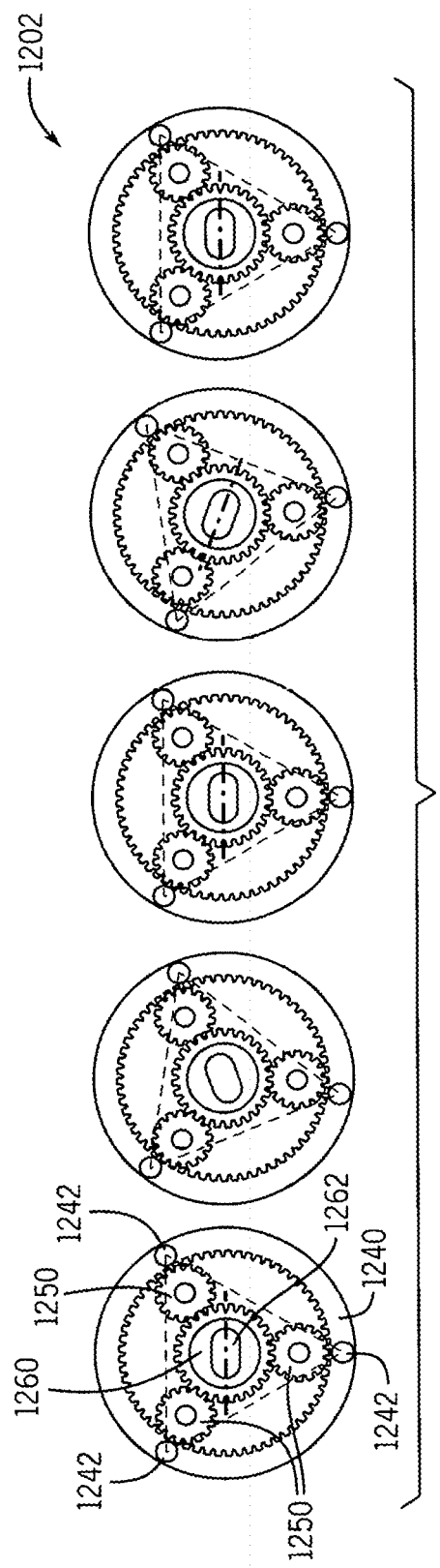

Row 4 of the above chart represents a still further variation of the operating principle of the embodiment described above. When a rotating motion source is available, it can cause a connector in a TENS attachment also to rotate. The rotation can then be coupled to drive the rotor of a stepper motor generator, which can generate AC current at the outputs from the generator motor coils. Alternatively, the rotation of the motion source can be converted to an oscillation, which can then be applied to a stepper motor generator. (A mechanism for converting a rotary motion in to an oscillating motion is shown in FIGS. 12A-12C, which are adapted from U.S. Patent Application Publication 20160045081 for Device and Method for Cleansing and Treating Skin, Ser. No 14/825316 incorporated herein by reference.).

Further detail on the operation of such a mechanism is as follows. FIG. 12a is a partially exploded view of actuator mechanism 1, including features disposed within handle 1110 of cleansing device 1100. Actuator mechanism 1200 includes primary drive 1201 and secondary drive 1202. Primary drive 1201 includes motor drive shaft 1210, gear mechanism 1220 and pivot arm 1230. Motor drive shaft 1210 includes engagement member 1212, collar 1214, and collar gear 1216. Collar gear 1216 is attached to motor drive shaft 1210 and thus moves along with motor drive shaft 1210. Collar 1214 and engagement member 1212 are attached to each other but not to motor drive shaft 1210 and thus the collar 1214 and engagement member 1212 are able to move in a rotational manner independently of motor drive shaft 1210 and collar gear 1216. Gear mechanism 1220 includes gear 1222, offset pin 1224 (extending upwards from gear 1222 in FIG. 12A), and center pin 1226 (extending downward from gear 1222 in FIG. 2A. Gear 1222 is engaged with collar gear 1216 and is held stationary in space by center pin 1226 (that is, center pin 1226 is engaged with a stationary member, not shown). Pivot arm 1230 is attached to and is supported by collar 1214 and includes slot 1232 that is slidably engaged with offset pin 1224. Secondary drive 1202 includes outer ring gear 1240, planetary gears 1250, and sun gear 1260. Outer ring gear 1240 includes engagement pins 1242. Sun gear 1260 includes engagement slot 1262 that is adapted to receive engagement member 1212. Sun gear 1260, planetary gears 1250, and outer ring gear 1240 combined to form a planetary gear system.

When engagement member 1212 is operably engaged with engagement slot 1262, primary drive 1201 and secondary drive 1202 are operable to provide counter-oscillatory movement by virtue of moving collar gear 1216 by the rotational motion of the motor turning the shaft 1210. This movement is shown in FIGS. 12B and 12C. FIG. 12B is a top-down view of the primary drive 1201. One full cycle of movement of primary drive 1201, driven by the motor turning collar gear 1216, is shown from left to right in FIG. 12B. Movement of shaft 1210 moves collar gear 1216 in a clockwise direction. Motion of gear 1222 in a counterclockwise direction occurs by engagement of collar gear 1216 with gear 1222. Rotation of gear 1222 causes movement of offset pin 1 within slot 1232, urging pivot arm 1230 to move in a first counterclockwise, then clockwise, then counterclockwise movement as shown by the left-to-right series of configurations in FIG. 12B. In some embodiments, the arcuate movement of pivot arm 1230 over a single complete cycle as shown in FIG. 12B traverses an arc of about 20° to 50° or about 25° to 45., or about 30° to 40°. Engagement member 1212 moves contemporaneously and over the same arc as that described by the pivot arm 230. FIG. 12C is a top-down view of the motion of secondary drive 1202 when engagement member 1212 of primary drive 1201 is engaged within engagement slot 1262. One full cycle of movement of primary drive 1202, driven by the actuator engaged with primary drive 1201, is shown from left to right in FIG. 12C. Dashed lines are provided to add perspective regarding the relative movement of sun gear 1260 and pins 1242 attached to outer ring gear 1240. Movement of sun gear 1260, engaged with planetary gears 1250, acts to move outer ring gear 1240 in an opposing direction to the movement of sun gear 1260, as shown by motion of pins 1242. The movement of outer ring gear 1240 over a single complete cycle as shown in FIG. 12C traverses an angle of about 5° to 30°, or about 7° to 25° or about 10° to 20°.

As known from row 1, the AC current from the stepper motor can be can be rectified and processed in power boost and logic supply circuitry to provide sufficient electrical current to power a TENS signal generator circuit, capable of producing an aesthetic or other TENS waveform.

Row 5 of the above chart represents a still further variation of the operating principle of the embodiment described above. When a rotating or oscillating motion source is available, it can cause a connector in a TENS attachment also to rotate. The rotation or oscillation can be coupled to a mechanism for striking, compressing or otherwise deforming a piezoelectric crystal, for example a quartz crystal. Quartz is piezoelectric, which means that the material generates a voltage and charge when deformed.

This piezo-driving mechanism may for example tense and release a spring to drive a striker, as in a known piezo-based ignition device, to deliver a high voltage current pulse. A sudden forceful deformation of piezo material produces a high voltage and subsequent electrical discharge. Such discharges may be repeatedly generated and captured in a capacitor. Alternatively, the deformation can be delivered (e.g., by a cam in contact with a flexible array of piezoelectric devices, such as in a wearable power generating fabric. Deforming the piezoelectric devices provides charge to a capacitor. (See, "Powerful curved piezoelectric generator for wearable applications", Woo Suk Jung, Min Jae Lee, Min Gyu Kang, Hi Gyu Moon, Seok Jin Yoon, Seung Hyub Baek, Chong Yun Kang, KU-KIST Graduate School of Converging Science and Technolog, https://koreauniv.pure.elsevier.com/en/publications/powerful-curved-piczoelectric-genertor-for-wearable-applications). The stored charge from piezo action can be accumulated and provided to a boost supply circuit and then to a logic supply circuit. As known from row 1 of the chart, a resulting AC current from repeated piezo deformations can be can be rectified and processed in power boost and logic supply circuitry to provide sufficient electrical current to power a TENS signal generator circuit, capable of producing an aesthetic TENS waveform.

Alternative Using Electrical Power Tapped from Handheld Device.

In one embodiment, the step of mechanical conversion of energy may be avoided and electrical energy available in the handheld device 100 may be more directly accessed. Here, the design is to have a connector in the handheld device 100 that allows two separate states. One state of the connector supplies current to the motor of the motion source in the handheld device. (This is the normal cleansing motion state.) In the second, current supply for the motion source is interrupted and electric power from a source in the handheld device is supplied to circuitry in the TENS attachment.

Figure 11A:
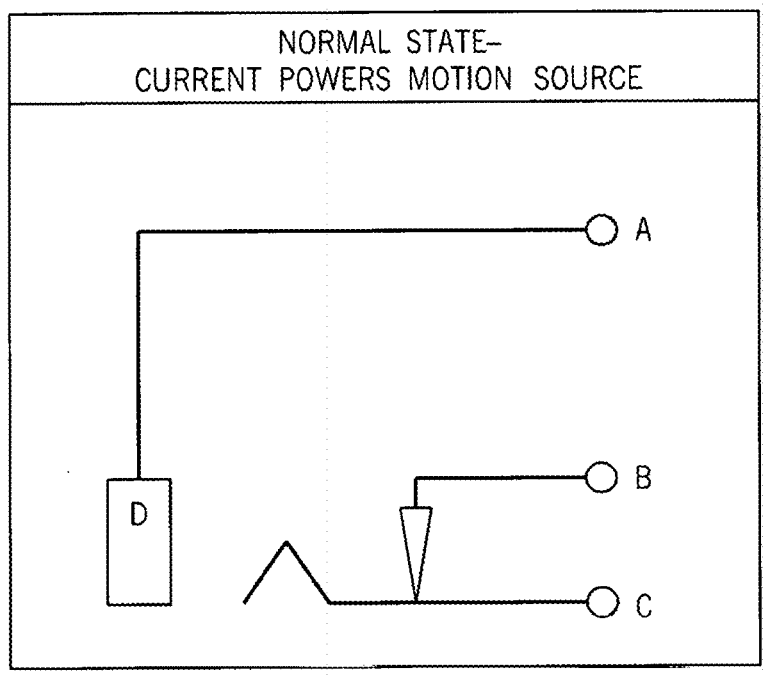
FIG. 11A is a schematic diagram of a jack connector that can be used in the handheld device to allow a jack in a TENS attachment, upon insertion, to disconnect power supplied to a motion source in the handheld device and also make a connection to an electrical source within the handheld device, so that this electrical source powers TENS signal generating circuitry in the TENS attachment.

In one embodiment, a jack-type connector with a spring contact that allows switching states may preferably be used. FIG. 11A show a schematic diagram of an audio jack type connector 270 designed to disconnect a current supply path to a speaker when a jack for earphones is inserted. In FIG. 11A such a connector 270 is used in the current supply path for the motion source; the current supply path includes the path B to C, which is normally conductive, Such a jack connector 270 can be placed at the connection interface between the mounting portion 130 of the handheld device and the TENS attachment 200. The TENS attachment 200 may be configured with a jack 260 for inserting into the connector 270 when the TENS attachment 200 is placed on the mounting portion 130.

Figure 11B:
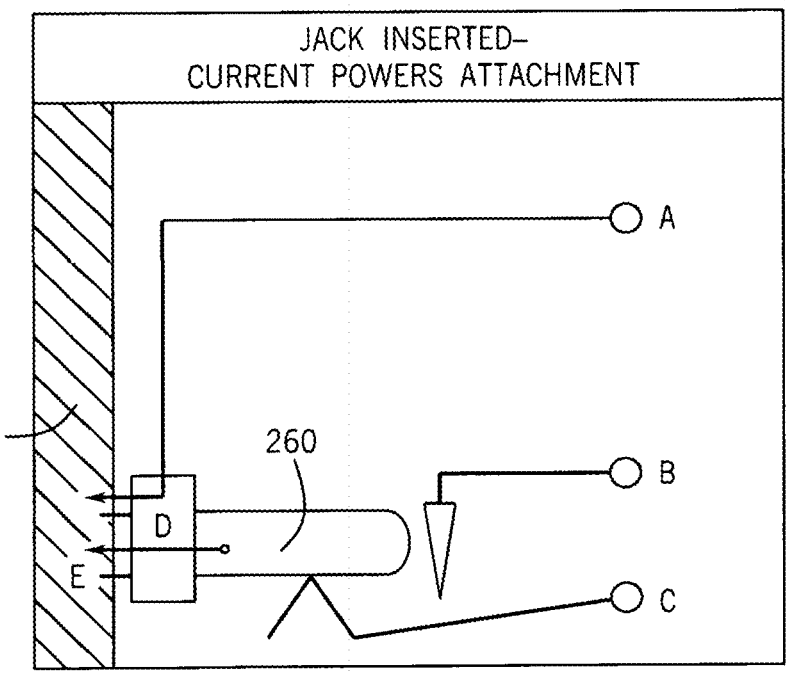
FIG. 11B is a schematic diagram of the jack connector of FIG. 11A in the state where a jack of a TENS attachment has been inserted to disconnect power supplied to the motion source in the handheld device and also make a connection to the electrical power source within the handheld device, so that electrical source supplies power to TENS signal generating circuitry in the TENS attachment.

As can be seen in FIG. 11A, if the circuit feeding current to the motor that drives the motion source is connected such that the spring contacts cause the current feeding circuit to be completed in the absence of an inserted jack 260, then the current supply to the motion source exists whenever no jack is inserted. As can be seen in FIG. 11B, insertion of a jack 260 associated with a TENS attachment deforms the spring contact so that the B-C current-feeding path for the motion source is broken. Upon the breaking of this circuit, another circuit is formed that allows the inserted jack 260 to form a circuit between points A and C, which may connected to the poles of a battery or some other current source in the handheld device 100 (preferably via the switch 120). The energy from A-C feeds to current supply pair D-E, leading into the TENS attachment. This current source at pair D-E leading into the TENS attachment can then be boosted or reduced as needed to match the TENS waveform generating circuit in the TENS attachment and support its production of the TENS waveform. Meanwhile any motion of the motion source has been stopped, because the motor driving it has temporarily (during jack insertion) lost its power supply. Removal of the TENS attachment with its jack 260 restores the normal supply of current to the motor for the motion source.

Use of the Device; Alternative Hand Contact

The cleansing device for which the TENS attachment is designed is used to cleanse the skin of a mammal; in particular, the skin of a human. In some embodiments, the basic handheld device is used as a facial skin cleanser for a human. The device is intended to be used in conjunction with a skin cleansing composition, for example a detergent or non-detergent facial skin cleansing composition. To use the device, a user coats at least a portion of the cleansing head first major surface with a skin cleansing composition (or alternatively applies the composition to a skin area), contacts the device to his or her own face, and turns the device on to start a skin-stretching movement caused by the displacement between head sections caused by oscillation of the motion source.

Without wishing to be limited by theory, we believe that a specific degree, frequency, or period of controlled stretching of the human skin, or combination of two or more thereof, results in micro-extracellular matrix stretching that in turn causes stretching of the attached dermal fibroblasts. Such stretching, we believe, causes favorable gene expression changes in the fibroblasts, directing them to repair or augment the extracellular matrix (ECM) of the skin and improve skin health and appearance. The extracellular matrix is composed of collagen fibers, elastin fibers, and the water-holding molecules retained within the network of the fibers, for example other proteins and gycosaminoglycans such as chondroitin, biglycan, hyaluronic acid, and the like. Restoring the ECM results in an improvement in appearance and a decrease in the apparent age of the subject.

It is further believed that following a cleansing action of this type it is particularly effective to have a TENS treatment to take advantage of the beneficial effects of the cleansing. Thus, the cleansing head can be removed and replaced by the TENS attachment after the cleansing session is finished. For the TENS attachment with the first and second electrodes 222, 224 as seen in FIGS. 8B, 8C, both electrodes must touch the skin to form a current path over which the TENS waveform is delivered, traveling between the first and second electrodes.

A somewhat different current path can be established if a conducting surface is available on the handle 110 of the handheld device 100. Such a conducting surface can be used as one electrode, with the TENS attachment skin contact surface 210 then having a single treatment contact electrode. When the TENS attachment is configured to deliver the TENS waveform as a voltage between these two electrodes, the current path runs from the user's hand in contact with the conducting surface available on the handle 110 and along arm of the user to the skin contact surface 210 with the single treatment contact electrode, in contact with the face or other skin surface of the user. To set up this path, it is necessary for the conducting surface available on the handle 110 to be become part of the current path. For example the lighter-colored portion 150 of the handle 110, which runs up both sides of the handle (as seen in FIG. 2) to the mounting portion 130 may be a conductive plastic. This conductive portion may then be connected as one end of the circuit upon mounting of the TENS attachment 200, using a two-state connection jack similar to the one shown in FIGS. 11A-11B. Again, insertion of the jack can form a new current path that can run to the lighter-colored portion 150, which the user's hand will encircle. Alternatively, mounting the TENS attachment 200 could cause a conductive portion or element of the housing 212 (not shown) to make a connection to the lighter-colored conductive portion 150 of the handle 110. All that is necessary is that the user's normal hand position touches a conductive element that will become part of a circuit path between the two output wires of the output circuit 540 of FIG. 5 when the TENS attachment 200 replaces a cleansing head.

Various types of skin treatment and/or TENS conduction assisting compositions are useful in conjunction with the TENS treatment. In general, any liquid, dispersion, lotion, gel, serum, or solution conventionally used to improve conduction between skin and a TENS electrode can be used in conjunction with the TENS attachment During use, the TENS attachment is moved around the surface of the skin by the user and the TENS current flows through skin surfaces in conductive contact with an electrode. Examples of skin treatment or TENS conduction-assisting compositions usefully employed along with the TENS device include a Conductive Gel available from Nu Skin International, Inc. for use with a galvanic Facial Spa (Item 01003913).

Summary

The invention illustratively disclosed herein can be suitably practiced in the absence of any element which is not specifically disclosed herein. While the invention is susceptible to various modifications and alternative forms, specifics thereof have been shown by way of examples, and are described in detail. It should be understood, however, that the invention is not limited to the particular embodiments described. On the contrary, the intention is to cover modifications, equivalents, and alternatives falling within the spirit and scope of the invention. In various embodiments, the invention suitably comprises, consists essentially of, or consists of the elements described herein and claimed according to the claims.

Additionally each and every embodiment of the invention, as described here, is intended to be used either alone or in combination with any other embodiment described herein as well as modifications, equivalents, and alternatives thereof falling within the spirit and scope of the invention. The various embodiments described above are provided by way of illustration only and should not be construed to limit the claims attached hereto. It will be recognized that various modifications and changes may be made without following the example embodiments and applications illustrated and described herein, and without departing from the true spirit and scope of the claims.

The invention claimed is:

1. A device for delivery of TENS current, attachable to a handheld skin treatment device with a mechanical motion source, comprising:
    a housing for mounting on the handheld skin treatment device, comprising a conductive skin contact head with first and second electrodes for delivering a TENS signal as a voltage established between the electrodes;
    a connector mounted in or on the housing and configured to interface with the mechanical motion source to receive the motion of the motion source;
    an energy converter in the housing to convert the motion into electrical current;
    a power control circuit for receiving the electrical current and converting it into at least one power supply output voltage; and
    a signal generation circuit connected to the at least one power supply output voltage for producing as an output the TENS signal for delivery to skin.

2. The device of claim 1, where the signal generation circuit comprises a microprocessor that is configurable to determine one or more parameters of the TENS signal to make it a waveform suitable for aesthetic TENS treatment.

3. The device of claim 1, wherein the handheld skin treatment device comprises:
    a handle with a mounting portion for receiving a skin cleansing head, said head being removably connectable to the mechanical motion source; and
    wherein the housing is configured to support the first and second electrodes in a generally planar configuration for skin contact.

4. The device of claim 3, wherein the energy converter comprises a stepper motor and the connector configured to interface with the mechanical motion source receives an arcuate motion for delivery to the rotor of the stepper motor.

5. The device of claim 1 wherein the handheld skin treatment device is a device with an oscillatory mechanical motion source for delivery to a removable head that translates the oscillatory mechanical motion into a relative motion between a first portion of an elastomeric skin contact surface and a second portion of an elastomeric skin contact surface.

6. The device of claim 1 where the mechanical motion source is a shaft oscillating on an axis, the energy converter comprises a stepper motor and the connector configured to interface with the mechanical motion source receives from the shaft an oscillating arcuate motion for delivery to the rotor of the stepper motor.

7. The device of claim 1 wherein the energy converter is a pancake stepper motor.

8. The device of claim 1 wherein the TENS signal is a waveform consisting of a sequence of pulses of a one polarity followed by a sequence of pulses of an opposite polarity.

9. The device of claim 1 wherein the first electrode is in the form of a circle and the second electrode is in the form of a ring surrounding the circle.

10. The device of claim 1, wherein motion source provides arcuate motion, oscillating between the ends of an arc of between 5 and 90 degrees.

11. The device of claim 1, wherein the handheld skin treatment device comprises:
    a handle with a mounting portion;
    an electrical motor disposed within the handle and attached to an actuator, said motor and actuator adapted to supply an oscillating movement at a frequency of about 5 Hz to 30 Hz; and
    a cleansing head operably connected to the actuator and having a first major surface and a second major surface, the first major surface comprising a plurality of elastomeric cleansing features extending away from the first surface and having an aspect ratio of about 1:5 to 10:1,
    wherein the actuator is operably connected to the second major surface of the cleansing head to apply oscillating movement thereto, wherein the oscillating movement provides a total displacement per oscillation of about 0.5 mm to 8 mm.

12. The device of claim 11, wherein the cleansing head is partitioned into two or more cleansing head sections.

13. The device of claim 1, wherein the motion source provides one of oscillating or rotating motion.

14. A device for delivery of TENS current, attachable to a handheld skin treatment device with a mechanical motion source and a jack connector, comprising:

a housing for mounting on the handheld skin treatment device, comprising a conductive skin contact head with first and second electrodes for receiving a TENS signal as a voltage established between them;

a connection jack mounted in or on the housing and configured for insertion in the jack connector to interrupt a current that powers the motion source and direct a current from an electrical power source of the handheld skin treatment device to a current supply pair leading into the TENS attachment; and a signal generation circuit connected to the current supply pair for producing as an output the TENS signal for delivery to skin.

15. The device of claim 14, wherein the connection jack upon insertion displaces a resilient element that normally completes a current path of the current that powers the motion source.

16. A device for delivery of TENS current, attachable to a handheld skin treatment device with a mechanical motion source, comprising:

a housing for mounting on the handheld skin treatment device, comprising a conductive skin contact head with a first electrode for delivering a TENS signal as a voltage established between the first electrode and a second electrode;

a connector mounted in or on the housing and configured to interface with the mechanical motion source to receive the motion of the motion source;

an energy converter in the housing to convert the motion into electrical current;

a power control circuit for receiving the electrical current and converting it into at least one power supply output voltage; and a signal generation circuit connected to the at least one the power supply output voltage for producing as an output the TENS signal for delivery to skin from the first and second electrodes.

17. The device of claim 16, where the second electrode is located on the handheld skin treatment device so as to be contacted by a hand of a user and is connected to the TENS signal when the housing is mounted on the handheld skin treatment device.

* * * * *